United States Patent
Hardy et al.

(10) Patent No.: US 10,726,099 B2
(45) Date of Patent: Jul. 28, 2020

(54) SYSTEM AND METHOD FOR PROVIDING REAL TIME CONTROL OF PHARMACEUTICALS

(71) Applicant: Capsa Solutions LLC, Columbus, OH (US)

(72) Inventors: Rody Hardy, Columbus, OH (US); Eric Webb, Vancouver, WA (US); Andrew Sherrill, El Segundo, CA (US); Scott Salmon, Clackamas, OR (US); Dave Burns, West Linn, OR (US)

(73) Assignee: CAPSA SOLUTIONS LLC, Columbus, OH (US)

( * ) Notice: Subject to any disclaimer, the term of this patent is extended or adjusted under 35 U.S.C. 154(b) by 524 days.

(21) Appl. No.: 14/134,850

(22) Filed: Dec. 19, 2013

(65) Prior Publication Data

US 2014/0172447 A1    Jun. 19, 2014

Related U.S. Application Data

(60) Provisional application No. 61/739,134, filed on Dec. 19, 2012.

(51) Int. Cl.
*G06F 19/00* (2018.01)
*G07F 17/00* (2006.01)
*G07F 9/00* (2006.01)

(52) U.S. Cl.
CPC .......... *G06F 19/3462* (2013.01); *G07F 9/002* (2020.05); *G07F 17/0092* (2013.01)

(58) Field of Classification Search
CPC .................. G06Q 50/22; G06Q 50/24; G06F 19/322–327; G06F 19/00; G06F 19/10; G06F 19/30; G06F 19/70; G06H 80/00
See application file for complete search history.

(56) References Cited

U.S. PATENT DOCUMENTS 4,785,969 A    11/1988    McLaughlin
5,014,875 A    5/1991    McLaughlin et al.
(Continued)

OTHER PUBLICATIONS

For the Mommas Real Savings Real Solutions, webpage—https://forthemommas.com/?s=take+%26+Toss, Jan. 13, 2016, 2 pages.

*Primary Examiner* — Reginald R Reyes
(74) *Attorney, Agent, or Firm* — Standley Law Group LLP; Adam J. Smith; Jeffrey S. Standley

(57) ABSTRACT

Disclosed herein is a system for providing a user with remote real time access to pharmaceuticals, the system comprising a plurality of carts which accept cassettes that contain pharmaceuticals. The carts preferably contain a CPU which can communicate with a database. A remote CPU is also in electrical communication with the database and may be placed at a pharmacy. When a specific pharmaceutical is required for a specific patient, a user can electronically request a one time access code (OTAC) from the remote CPU. If the request is valid, an OTAC can be sent both electronically to the database in addition to being sent to the user. If the user inputs an OTAC that matches the one stored on the database, the cart is unlocked to provide access to the requested pharmaceutical. Pharmaceuticals that are currently found in the cart can be checked remotely by communicating with the database. A new cassette can then be stocked and sealed by a pharmacist, while another person can transmit the sealed cassette and replace the old cassette within the cart.

8 Claims, 33 Drawing Sheets

(56) References Cited

U.S. PATENT DOCUMENTS

| | | | |
|---|---|---|---|
| 5,258,906 A * | 11/1993 | Kroll | G06Q 20/127 |
| | | | 379/106.02 |
| 5,292,029 A | 3/1994 | Pearson | |
| 5,314,243 A | 5/1994 | McDonald et al. | |
| 5,377,864 A | 1/1995 | Blechl et al. | |
| 5,480,062 A | 1/1996 | Rogers et al. | |
| 5,713,485 A | 2/1998 | Liff et al. | |
| RE35,743 E | 3/1998 | Pearson | |
| 6,039,467 A | 3/2000 | Holmes | |
| 6,151,536 A | 11/2000 | Arnold et al. | |
| D631,348 S | 1/2011 | Weiss et al. | |
| 8,286,827 B2 | 10/2012 | Yacktman | |
| 2002/0165641 A1 | 11/2002 | Manalang et al. | |
| 2003/0201697 A1 * | 10/2003 | Richardson | A47B 81/00 |
| | | | 312/209 |
| 2003/0216831 A1 * | 11/2003 | Hart | G06F 19/3418 |
| | | | 700/235 |
| 2005/0065645 A1 * | 3/2005 | Liff | G06F 19/3462 |
| | | | 700/241 |
| 2005/0269337 A1 | 12/2005 | McGrath | |
| 2007/0095846 A1 | 5/2007 | Goecke et al. | |
| 2008/0237247 A1 | 10/2008 | Mucci et al. | |
| 2010/0004780 A1 * | 1/2010 | Rickelhoff | A61G 12/001 |
| | | | 700/231 |
| 2011/0290817 A1 | 12/2011 | Weiss et al. | |
| 2018/0150613 A1 * | 5/2018 | Bossi | G06F 16/2358 |

\* cited by examiner

SYSTEM AND METHOD FOR PROVIDING REAL TIME CONTROL OF PHARMACEUTICALS

CROSS-REFERENCE TO RELATED APPLICATIONS

This application is a nonprovisional patent application and claims priority to provisional application 61/739,134, filed on Dec. 19, 2012 which is herein incorporated by reference in its entirety.

TECHNICAL FIELD

The disclosed embodiments of the present invention relate to a method and device for storing and dispensing medications and the like to patients prior to delivery of patient specific medications to a health care provider.

BACKGROUND AND SUMMARY OF THE INVENTION

Health care facilities such as nursing homes and assisted living facilities, frequently must administer pharmaceutical products to those individuals in their care, referred to as patients or care recipients hereinafter. Such facilities often rely on commercial pharmacies to provide these pharmaceutical products. These pharmaceutical products are frequently provided to these facilities as patient-specific inventories that consist of multiple-day's worth of dosages. When a new patient enters the care of such a facility there is often a lag between the time that the patient care begins and corresponding pharmaceutical products arrive. The current solution to this lag is to maintain a general inventory of pharmaceutical products at each facility in a divided storage box or other similar container. Some of the difficulties of such a system include: no accountability for access to drug inventory generally; regulatory issues related to access to narcotic drugs kept in such an inventory; maintaining sufficient inventory levels; and billing associated with dispensed drugs.

The present disclosure is directed to a drug and medical supply dispensation cart that may be connected using wired or wireless communications technology to a system and database that may track the inventory on such a cart, allow configurations of such a cart that are optimized for the site at which the cart is located, permit local user access to be managed by at least one administrative user located at the site or remotely, enable automated restocking and other remote management and configuration functions as described in more detail herein.

BRIEF DESCRIPTION OF THE DRAWINGS

A better understanding of the disclosed embodiments will be obtained from a reading of the following detailed description and the accompanying drawings wherein identical reference characters refer to identical parts and in which:

FIG. 7 is a screenshot of an exemplary embodiment of a pharmacy and system settings user interface;

FIG. 8 is a screenshot of an exemplary embodiment of a manage facility user interface;

FIG. 9 is a screenshot of an exemplary embodiment of a search and modify facility user interface;

FIG. 21 is a screenshot of an exemplary embodiment of a setup carts user interface;

FIG. 28 is a screenshot of an exemplary embodiment of an inventory report user interface;

FIG. 29 is a screenshot of an exemplary embodiment of a view cart log files user interface;

FIG. 30 is a screenshot of an exemplary embodiment of a manage user profile interface;

DETAILED DESCRIPTION OF A PREFERRED EMBODIMENT

Figure 1:
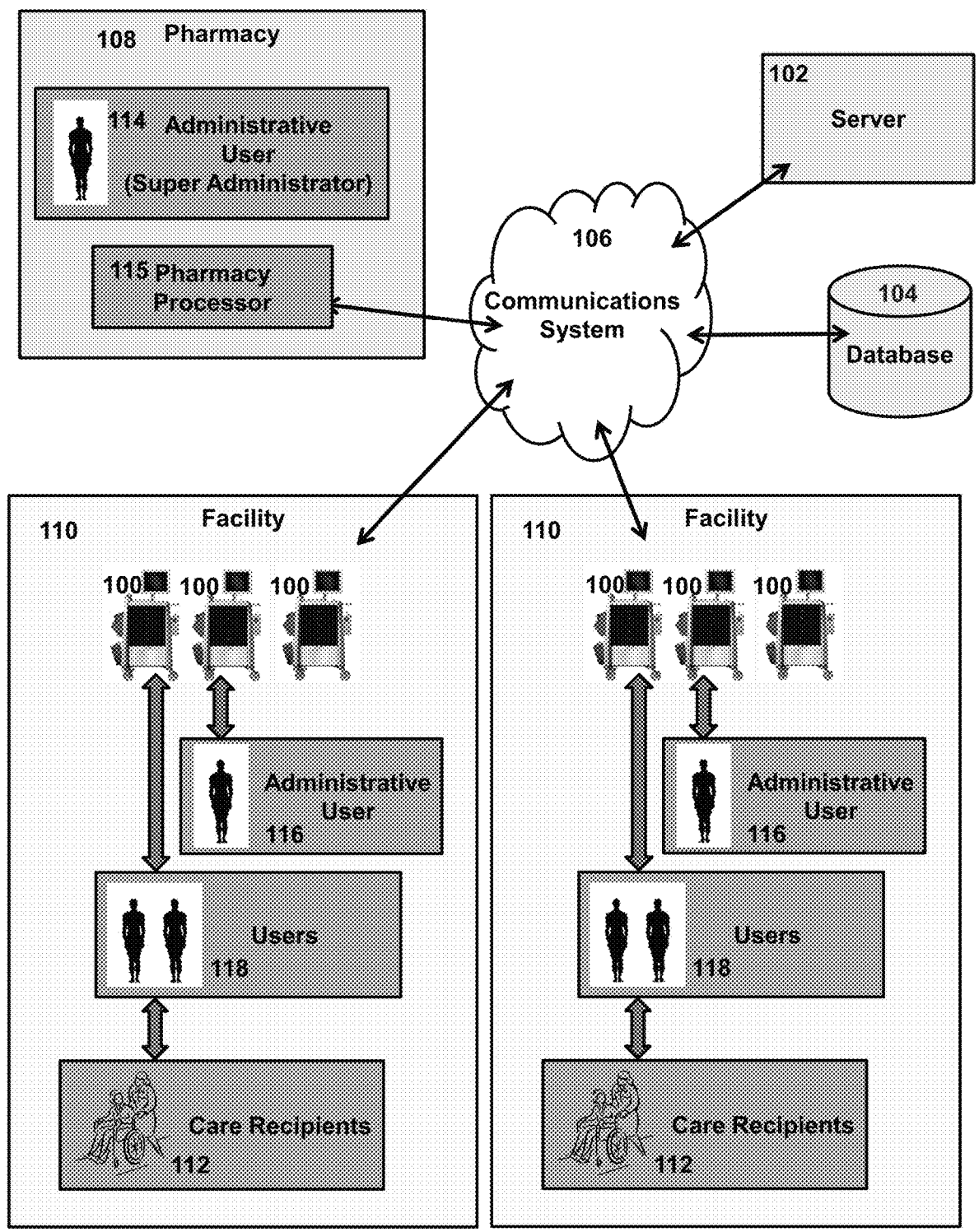
FIG. 1 is a schematic diagram of an exemplary embodiment of a real time pharmaceutical control system showing multiple care facilities.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

Like numbers refer to like elements throughout. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Referring to FIG. 1, the real time pharmaceutical control system (hereafter referred to as "real time pharmaceutical control system" or "system") may be comprised of a server 102, a database 104, and a plurality of drug supply and storage systems ("carts") 100. Each cart may be equipped with a computing device that controls access to drugs and supplies contained within the cart. In addition to a computing device, each cart may contain electronics comprising a processor, memory, a mechanism in communication with said processor to control access to areas of the cart, and a mechanism which may communicate with the computing device. In order to synchronize information comprising cart setup, cart inventory, cart logs, user privileges, and drug lists between the various components of the real time pharmaceutical control system, a communications system 106 may be employed. Such a communications system may comprise wired connections between carts and other components of the system but may also comprise one or more wireless communication methods. Drug supply and storage system carts may be obtained from CAPSA Solutions of Columbus, Ohio (www.capsasolutions.com, Artromick AC Medication Cart).

Figure 2:
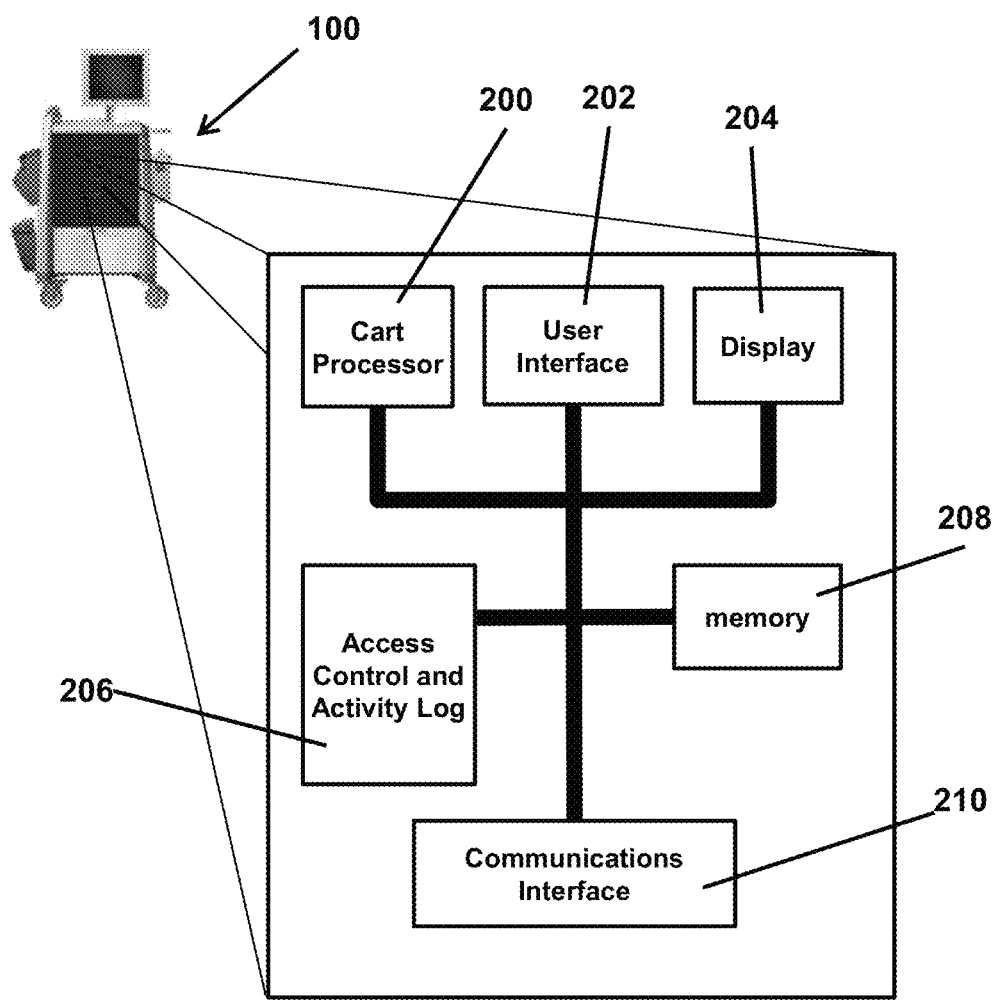
FIG. 2 is a schematic diagram of an exemplary embodiment of a cart.

Referring to FIG. 2, a cart 100 may comprise a cart processor 200, a user interface 202, a display 204, access control and data logging hardware 206, memory 208, a communications interface 210, and software. The cart processor 200 may be configured using software to send and receive data from the server 102 of the real time pharmaceutical control system. The cart processor 200 may also receive input from the user interface that reflects interactions between users 118 and the cart and its inventory. Such a user interface 202 may comprise a touch screen, keyboard, mouse or track pad, a card reader, or a barcode scanner. A communications interface 210 which may be comprised of electronic devices that enable electronic data communications between the cart 100 and wired or wireless embodiments of the communication system 106 may be used to provide data exchange between the server 102 and cart processors on deployed carts. The information sent and received by the cart processor may comprise access requests, access permissions, and cart inventory data. The exchange of such information may permit the cart, as a component of the system to function in the manner described herein. The cart processor 200 may also be in electronic communication with access control and activity logging hardware 206. The access control and data logging hardware 206 may control access to various cart storage locations and grant access to those locations upon receiving instruction from the cart processor. Embodiments of the invention may use devices such as magnetic and solenoid operated locks to secure cart storage locations. In some embodiments of the invention, the cart processor may receive log data from the access control and data logging hardware 206. Such data may comprise a record of cart storage compartment access and other user interactions.

Referring again to FIG. 1, an exemplary system preferably comprises a plurality of carts 100 in communication with a server 102 through the use of a communications system 106. The communications system may be in electronic communication with a server 102 device upon which management and control algorithms are executed and a database 104 which may be accessed by the server 102. Thus configured, the communications system 106 may permit information to be communicated between the various components of the exemplary real time pharmaceutical control system. The communication system 106 may comprise a computer network which may further comprise wired and wireless communications systems. In an exemplary embodiment the system may be associated with a pharmacy 108, a plurality of facilities 110 which provide care to care recipients 112. As is illustrated in FIG. 1, a pharmacy 108 may comprise a pharmacy processor 115 which may be a computer device including, but not limited to, a personal computer, a data terminal, a tablet computer, or a laptop computer. The database 104 may integrate data related to the contents of the plurality of drug and supply storage systems 100 and such users that interact with the supply storage systems. Super administrative users 114 and administrative users 116 may be associated with pharmacies 108 and facilities 110 respectively. These users may perform activities such as the setup of various parts of the exemplary real time pharmaceutical control system, maintenance, stocking of drugs and supplies stored in the drug and supply storage system(s) and dispensation of such drugs and supplies to care recipients 112.

Carts 100 may be organized with a consistent drawer and bin configuration with an identification array appropriate for locating contents, an example of which may be an alphanumeric grid. The real time pharmaceutical control system also may be configured to control user access to the drugs and supplies contained in carts. Such control may also include multiple levels of access control for certain items such as narcotic drugs.

The real time pharmaceutical control system preferably comprises management and control algorithms implemented as software. Such algorithms may comprise the following main components: Pharmacy Setup, Facility Setup Cart Design and Management, Inventory Management, User Creation and Management, User Access and Permissions, Data Synch between Pharmacy and Carts, and Reporting.

Figure 3:
FIG. 3 is an image of a user login interface.
Figure 4:
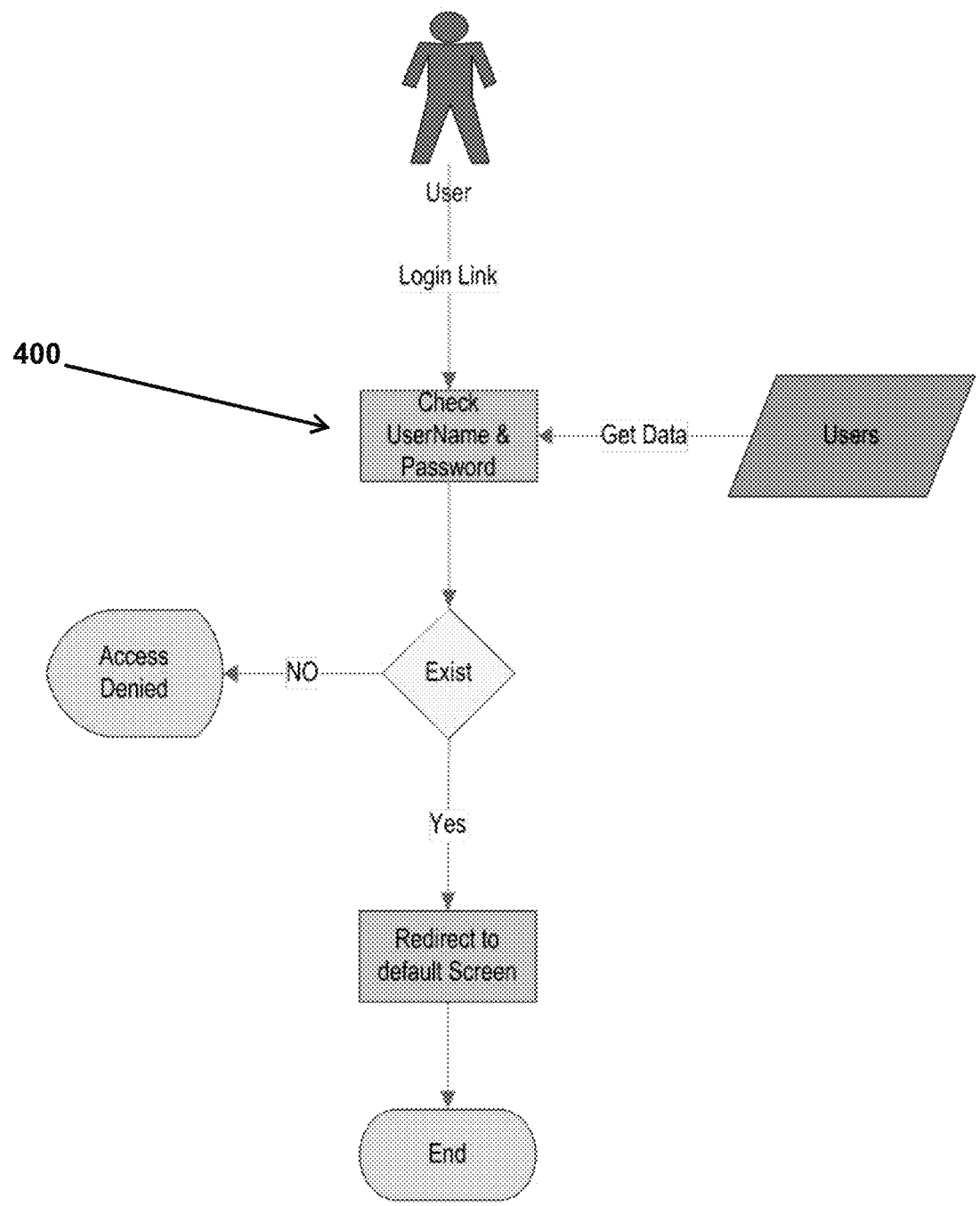
FIG. 4 is a flow diagram of one embodiment of the logic for the user login and verification process.
Figure 5:
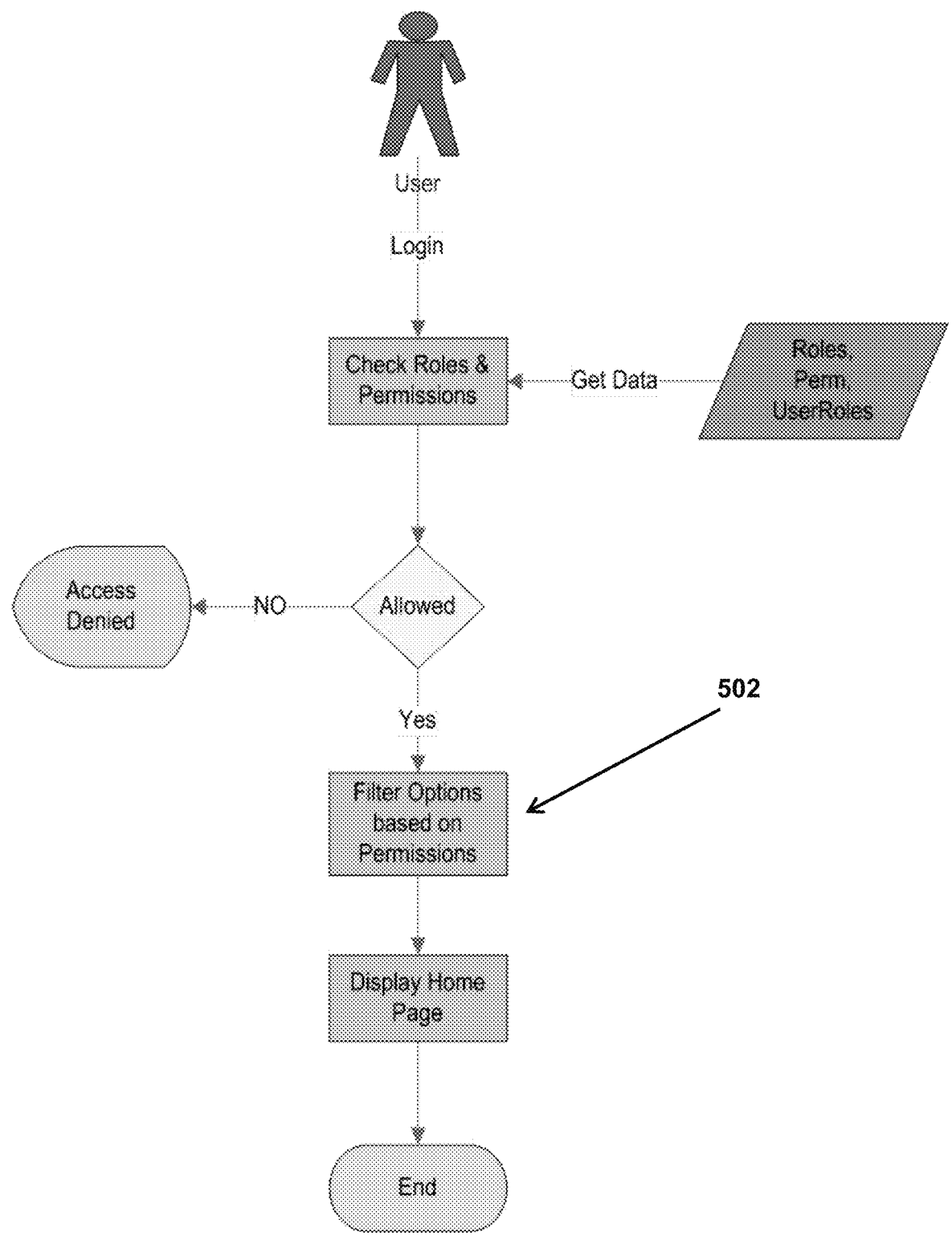
FIG. 5 is a flow diagram of an exemplary embodiment of the logic for performing a process used to configure displays based on user permissions.
Figure 6:
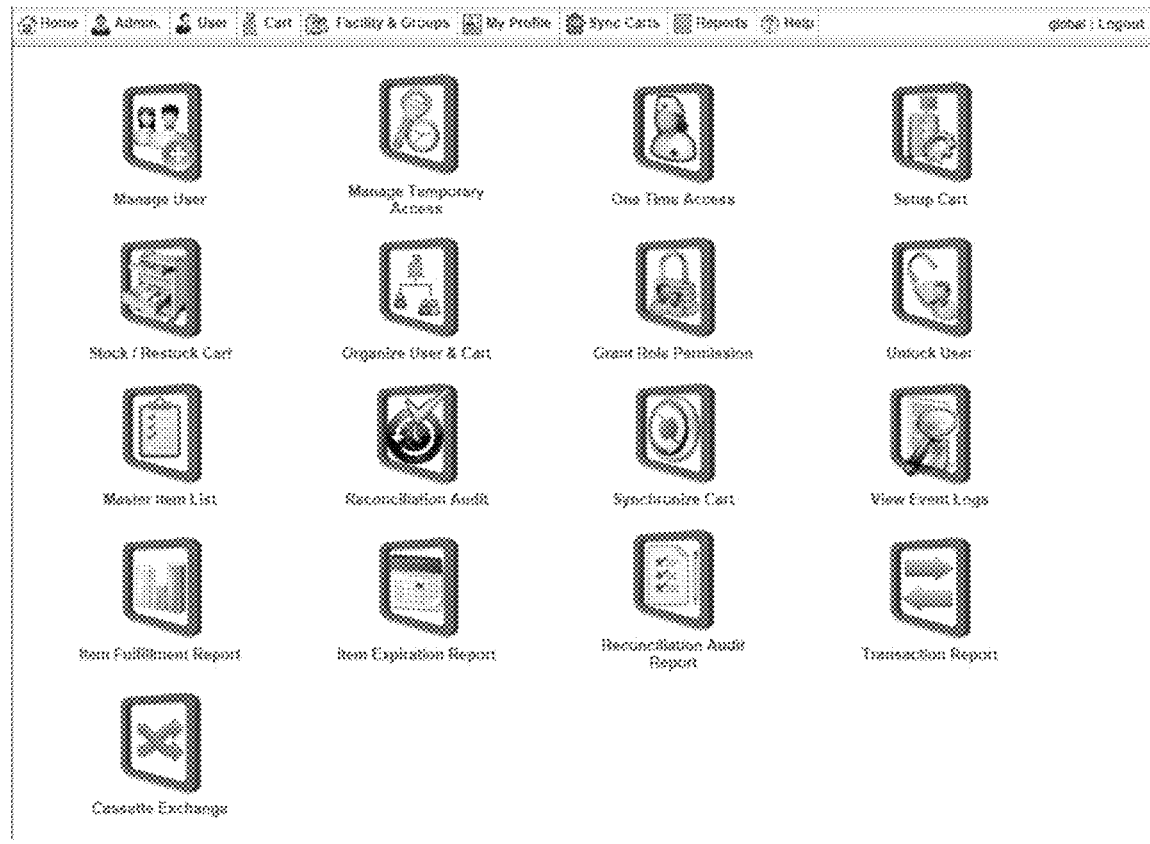
FIG. 6 is a screenshot of an exemplary embodiment of a main super administrator user interface.

A login function may be used to determine what level of access a user 118 is allowed for the real time pharmaceutical control System. A user 118 may enter a username and password using a login screen, an exemplary embodiment of which is illustrated in FIG. 3. Referring to the flow chart of FIG. 4, in step 400 the system may then check the username and password against those users contained in the database 104. If the username and password are not located, the user 118 may be prompted to re-enter the username and password. Assistance comprising "forgot password" or similar functionality may be implemented in order to improve the user experience. Referring to the flowchart of FIG. 5, if the username and password are located in the database, the system may configure a user interface "home page" based upon the type of access that the user 118 has been granted by a user with administrative authority. Such a home page has the effect of controlling user access to the information or drugs for which a user 118 does not have permission (see step 502). The home page may be presented to a user 118 upon initial login to the system and serve as a starting point for various interactions with the system. Referring again to FIG. 1, in an exemplary embodiment there are multiple levels of administrative permissions which may be granted to a user of the real time pharmaceutical control system. A user associated with a pharmacy 108 which is associated with an embodiment of the system may be granted administrator rights to all administrative functions of the system, such a user is referred to as a super administrator 114. A user with administrative rights 116 who is associated with facility 110 may have administrative rights limited to those administrative functions associated with the user's facility. Associated with each facility may be users with no administrative rights 118. An example of a super administrator's home page is shown in FIG. 6. A user with more limited access rights may be presented with a home page user interface which has fewer or different available selections.

From the exemplary home page illustrated in FIG. 6, administrators may access functions comprising: Facility Setup, Prepare Cart(s), Maintain Cart Inventory, connect to the carts to manage user and cart settings, and log records. Administrators may also use the system and its logic to change, add, or delete user and cart settings and apply data changes to such carts. Users with no administrative access can access some of the cart functions but may not have access needed to program carts or make changes to pharmacy or facility setups.

Figure 7:
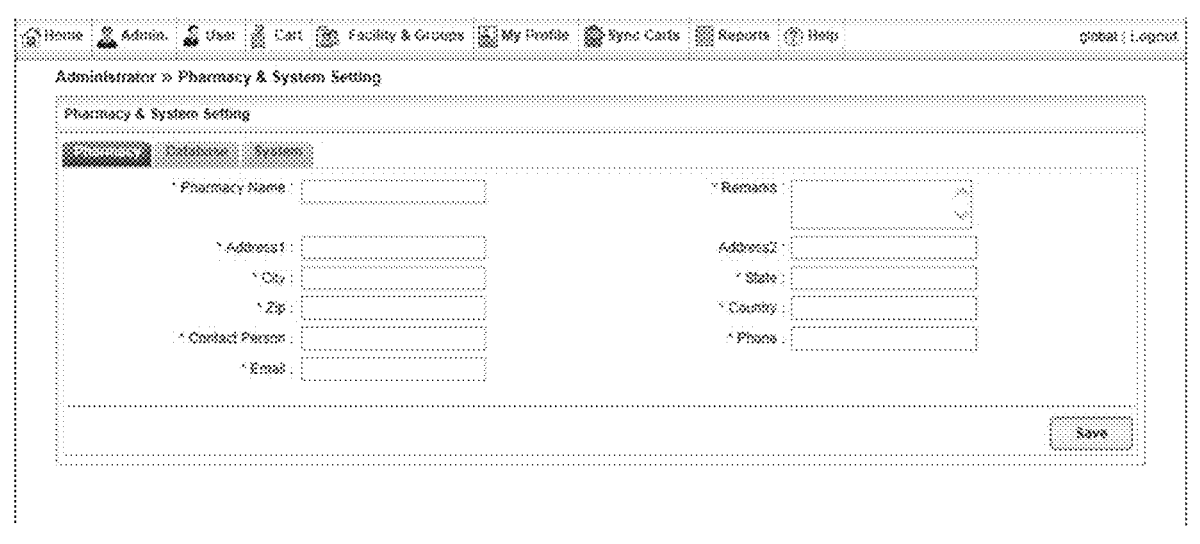

A pharmacy setup function is used to identify the pharmacy associated with a real time pharmaceutical control system. This association may only be modified by a user with super administrator rights. Users with non-super administrator rights may select the pharmacy setup option but may only view the information entered by a super administrator. From a pharmacy setup user interface screen, an exemplary embodiment of which is illustrated in FIG. 7, a super administrator may enter information about a pharmacy 108 comprising such information as pharmacy name, address, contact person, telephone and email ID. In addition, system settings can be updated or modified using this user interface which may include database settings, network settings, or software configuration customization settings.

Figure 8:
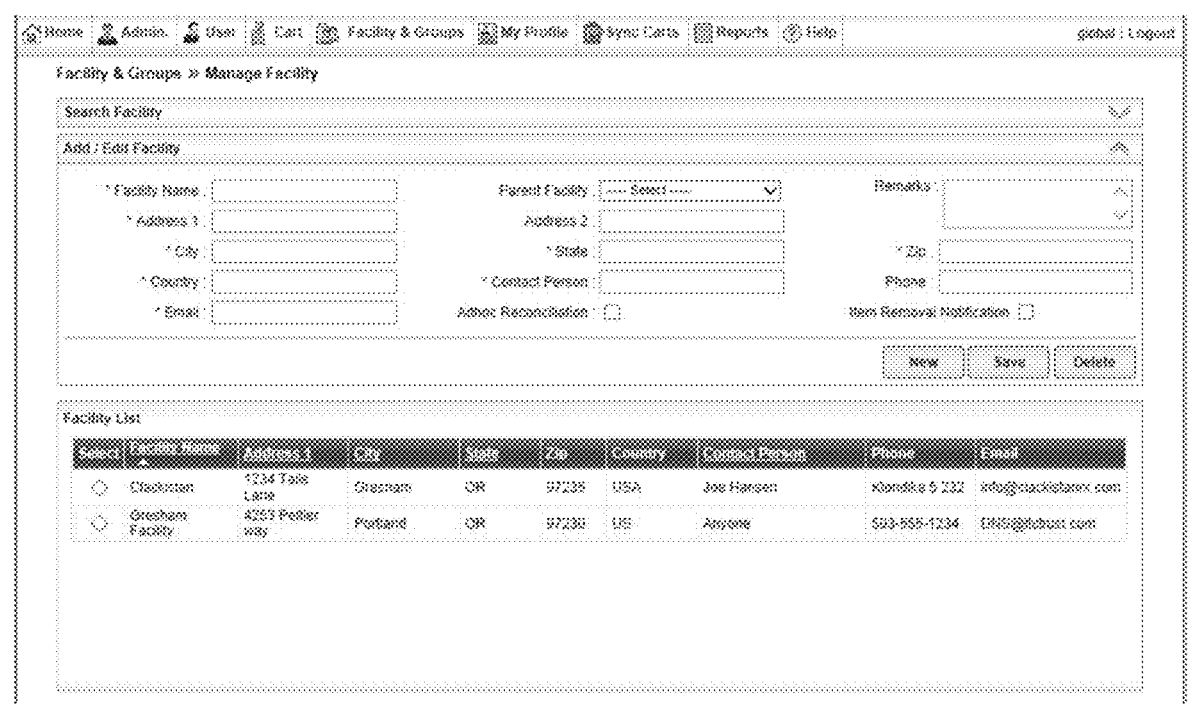

A facility setup function may be used to add a new facility to the real time pharmaceutical control system. Referring again to FIG. 1, a real time pharmaceutical control system may be configured to comprise a plurality of facilities 110, each with multiple carts 100, where each care provider provides care to multiple care recipients 112. Each facility may have a user with real time pharmaceutical control system administrative rights 116. The Facility Setup function allows a user with super administrative rights 114 or an administrative user 116 associated with a facility the ability to add new facilities or modify the information for existing facilities. A representative super administrator user interface for the facility setup function is illustrated in FIG. 8. In certain embodiments, a facility may have a subordinate facility which may be added from the facility setup function.

Figure 9:
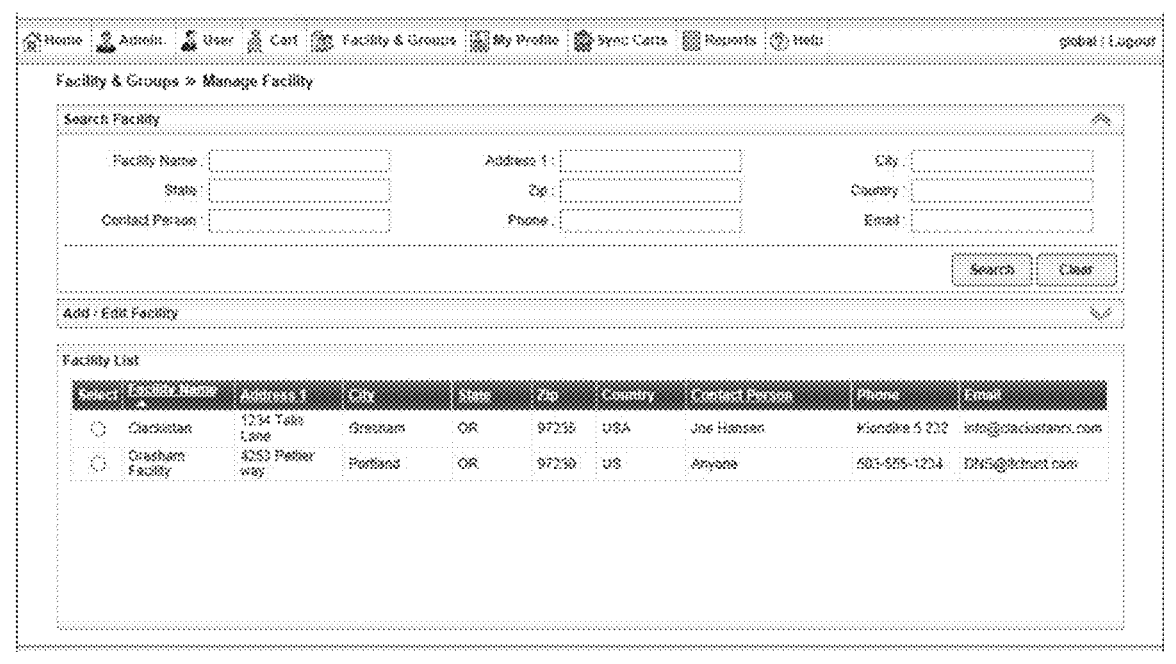

In addition to the facility setup function, a user associated with the pharmacy may also access a search facility function. A representative embodiment of a search facility user interface is illustrated in FIG. 9. Using this function, a user with administrative rights may search for facilities using characteristics that may comprise name, zip code, or city. An administrator may then select a facility and perform additional functions which may comprise editing the facility characteristics or deleting the facility from the real time pharmaceutical control system.

Figure 10:
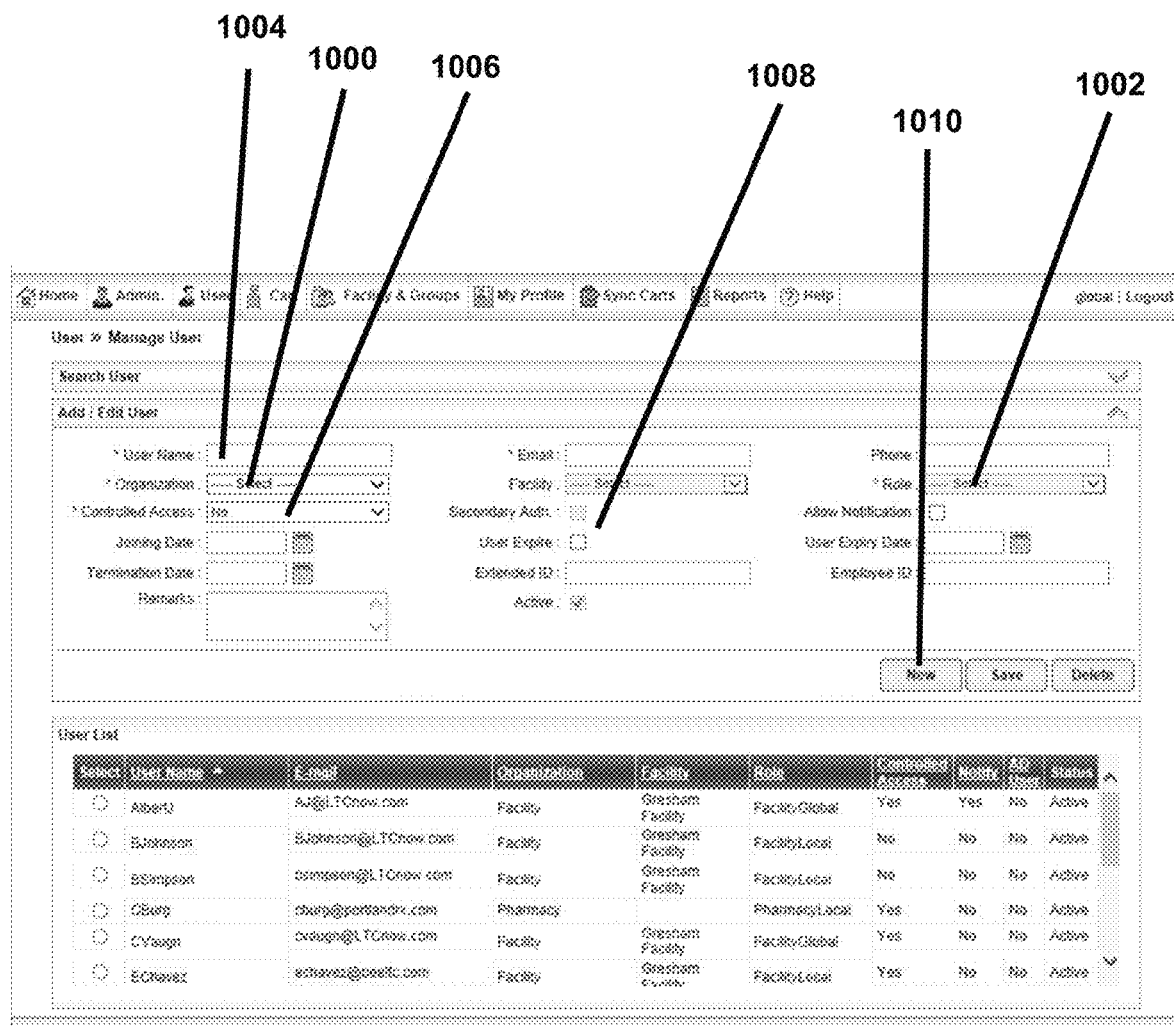
FIG. 10 is a screenshot of an exemplary embodiment of a manage user user interface.

Real time pharmaceutical control system users may be managed using a manage user function. A representative embodiment of a manage user interface is shown in FIG. 10. From this interface, an administrative user may search for users using characteristics that may comprise: user name; employee ID; facility; cart types associated with a user; other ID such as an email which may be assigned to a user; and a controlled item (narcotics) access identifier associated with a user. Using a manage user function, an administrative user may also add new users, edit an existing user, remove a user, or create and manage user groups from the manage user function. Access levels to controlled item storage locations for users may also be managed from this function.

Administrative users associated with a facility may add and edit users associated with that facility when such an administrative user selects the new user button 1010 from the manage user interface (FIG. 10). From this interface, a user with administrative rights may add a new user by entering information about the new user. This information may comprise: user organization 1000, the role 1002 for a user may determine access levels for that user, a unique user name 1004 user controlled item access permission 1006, and a selection to allow generation of a unique secondary authorization code for unlocking a controlled item storage area 1008.

Figure 11:
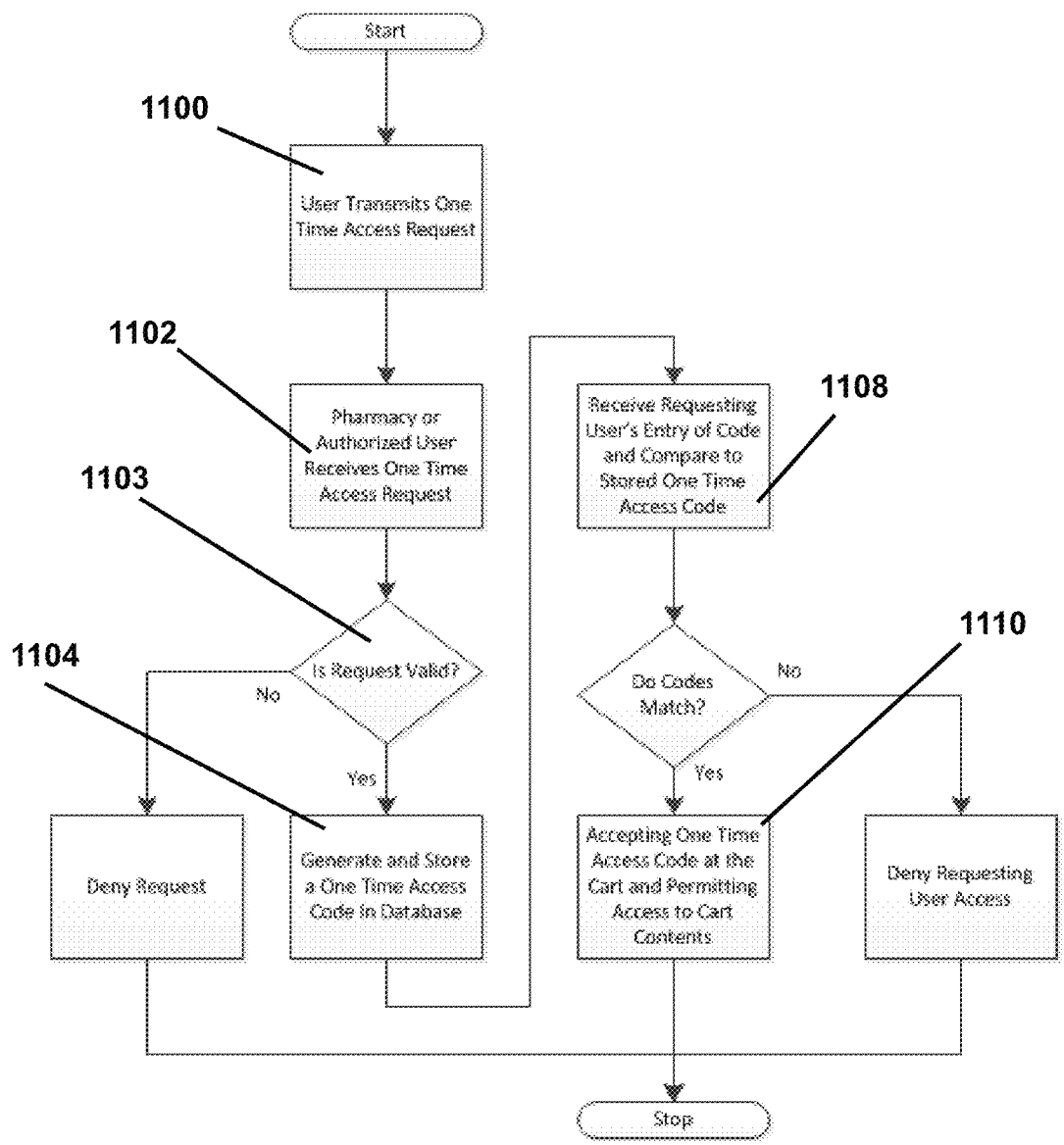
FIG. 11 is a flow diagram of an exemplary embodiment of the one time access request process.
Figure 12:
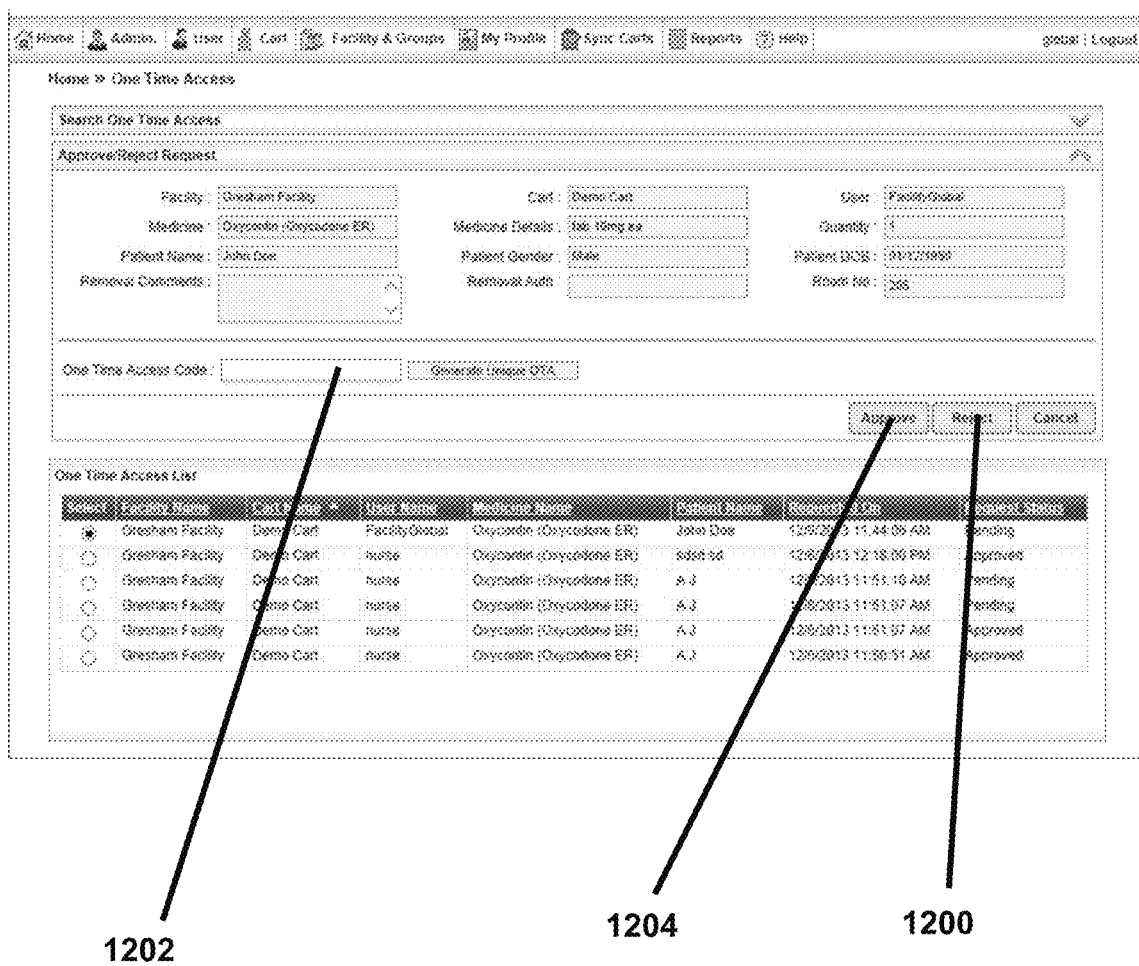
FIG. 12 is a screenshot of an exemplary embodiment of a manage temporary cart access user interface.

In some embodiments of the invention, users may request one time access to a cart. When a user wishes to request one time access, he or she enters information which may comprise facility name, user name, the date for which access is requested, medication type and quantity requested, and a patient or care recipient's name giving rise to the need for temporary access to a cart. Referring to the flow chart of FIG. 11, the user may transmit a one time access request using the real time pharmaceutical control system 1100, the request may be received by a pharmacy or other organization for review 1102, if the review indicates that such a request is valid 1103, the pharmacist or other authorized person may generate and store a one time access code 1104 in the database 104. The one time access code may also be communicated to the user using methods including, but not limited to, telephone calls, text messages, and email. Upon receiving the one time access code that user may enter the access code into the real time pharmaceutical control system user interface. The server 102 may compare the entered code to the stored one time access code 1108. If the compared codes match, the cart may permit the user to access the cart storage compartment which contains the required item or items 1110. When a user requests one time access, the real time pharmaceutical control system server 102 generates a notice to the person or persons authorized to grant the request. Referring to FIG. 12, upon receiving such a request, the user authorized to approve such a request, such as a pharmacist, may then either grant 1204 or reject 1200 the access request using the manage one time access function. A user may manually enter an access code 1202 or allow the server to generate an access code.

Figure 13:
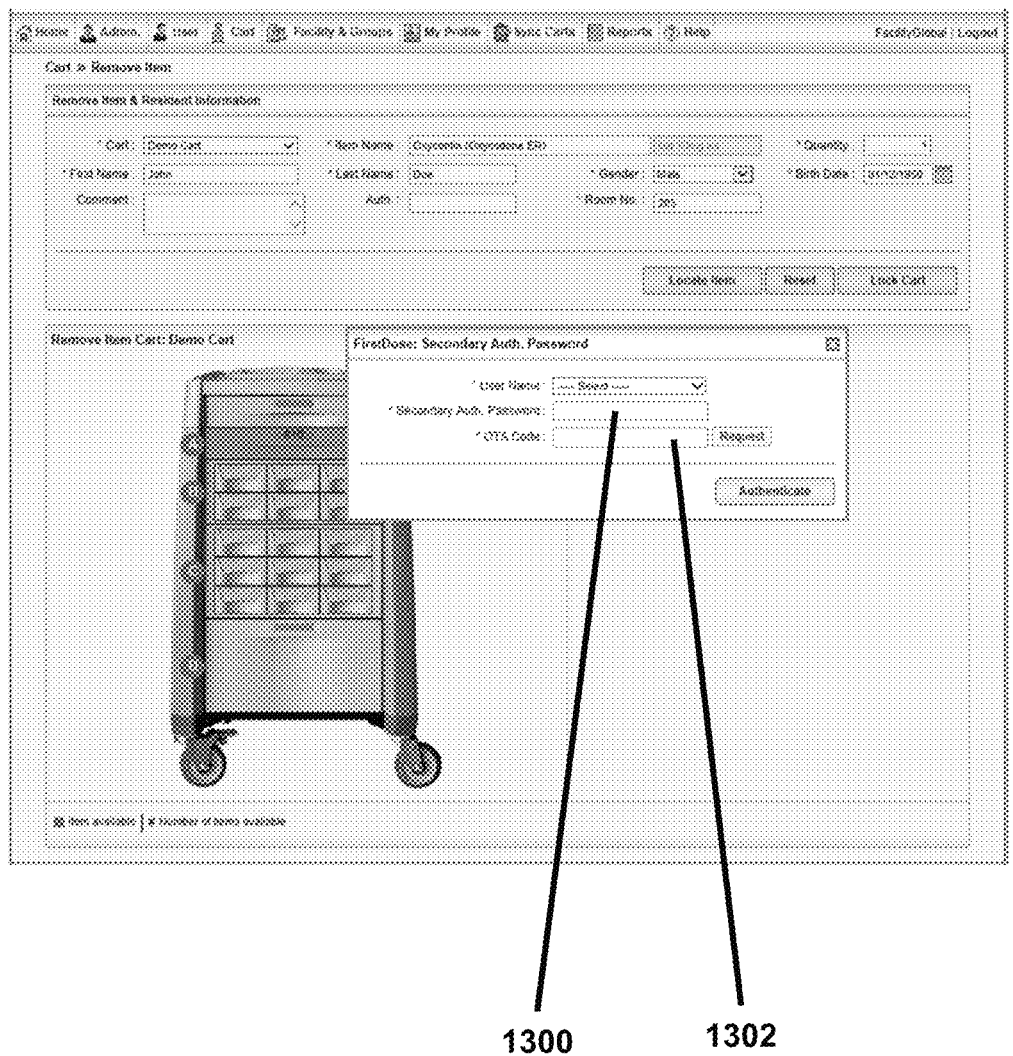
FIG. 13 is a screenshot of a temporary user access interface.

In another embodiment of the invention, access to certain cart contents may require a secondary authorization. Referring to FIG. 13, such an authorization may be the entry of a second user's password 1300 or entry of a one time access code 1202 which may be generated as the result of a request for access to those certain cart components which required a secondary authorization. Such an access code may be generated through a similar process to that described in the flow chart of FIG. 11. The code entered by the user on the interface shown in FIG. 13 at 1302 may be checked by the server 102 to ensure it matches the one time access code before allowing access to the cart.

As shown in the exemplary embodiment illustrated in FIG. 1, care provider facilities may have a plurality of supply storage systems ("carts") 100 associated with each facility. These carts may be configured or reconfigured as needed. In order to facilitate such configurations, the real time pharmaceutical control system may comprise cart design and management functions.

A master drug list function may be provided to allow for the creation and maintenance of a master drug list. This master drug list may be managed by the pharmacy and may then be used to select drugs to be deployed on carts. Drugs may be imported to and exported from the master drug list into other drug lists which may be stored in the database associated with the real time pharmaceutical control system.

Figure 14:
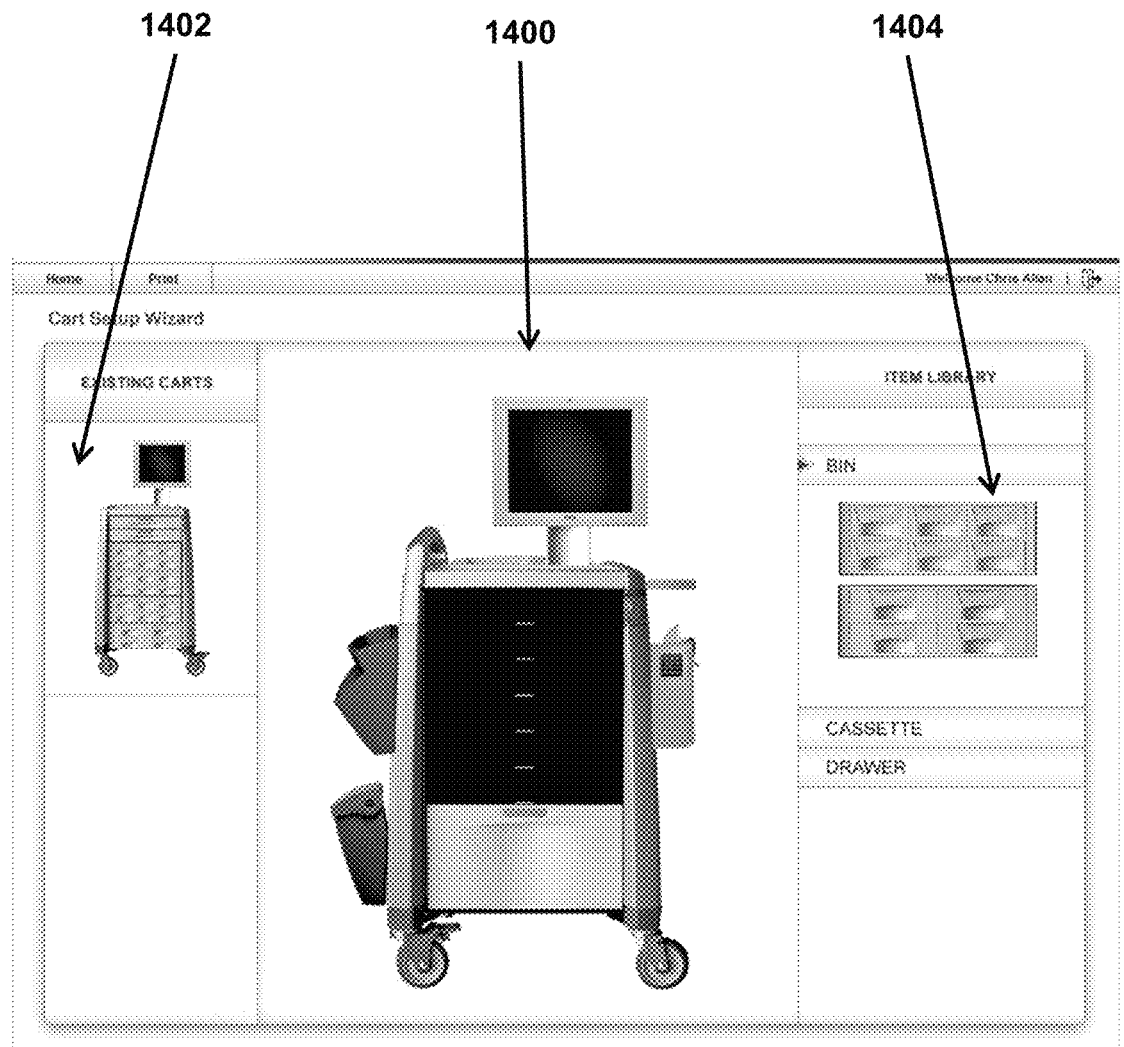
FIG. 14 is a screenshot of an exemplary embodiment of a cart setup wizard user interface.

When a new cart is added to the system, a user may use a cart setup wizard function to configure the cart. Referring to FIG. 14, an exemplary embodiment of such a cart setup wizard may comprise a visual representation of a cart 1400, a library of existing cart configurations 1402, and items which may be added to a cart such as storage drawers, bins, or cassettes 1404. Cassettes may comprise collections of drawers and bins. Using such a user interface, a user may configure or reconfigure a cart by dragging and dropping items into and out of the visual representation of the cart 1400.

Figure 15:
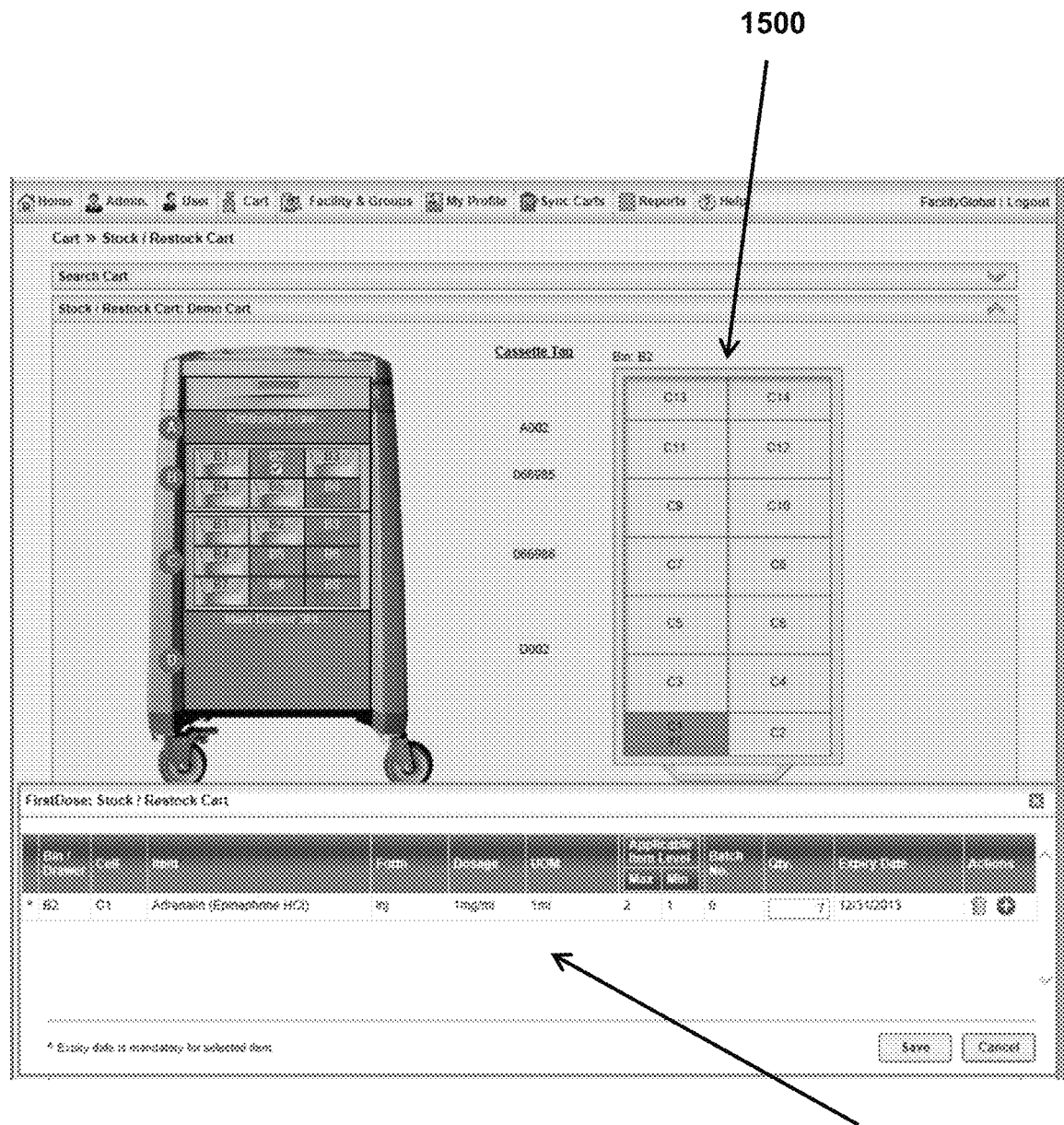
FIG. 15 is a screenshot of an exemplary embodiment of a stock/restock cart inventory user interface.
Figure 16:
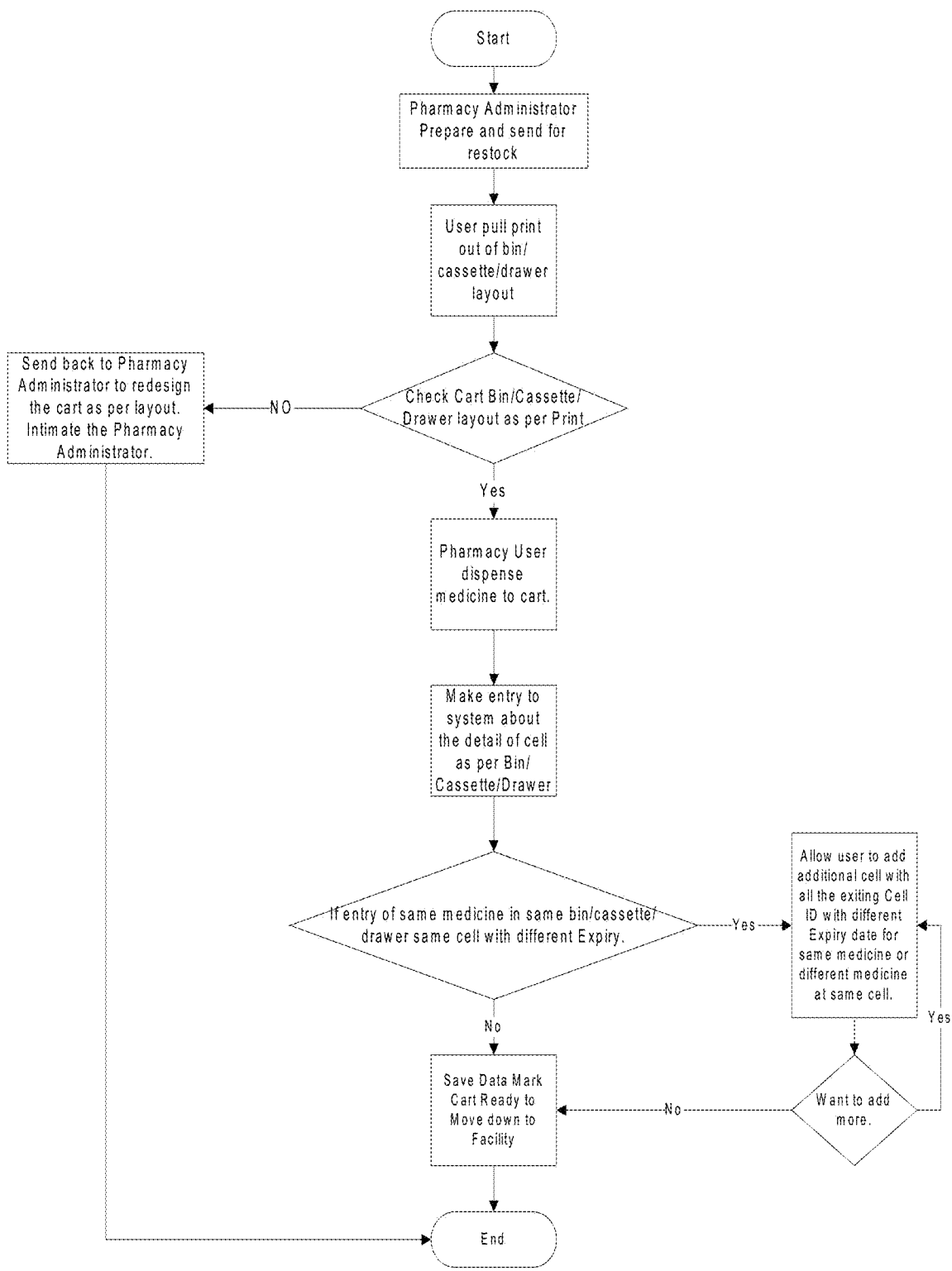
FIG. 16 is a flow diagram of an exemplary embodiment of the logic for performing a manage and restock cart inventory process.

An administrative user may setup the inventory of a new cart by copying the cart inventory template from an existing similarly configured cart, or by individually assigning medications to individual bins/cassettes/drawers. Referring to FIG. 15, a user may view an illustrative representative of bins/cassettes/drawers 1500 and the medications associated with each 1502. The user may then select a bin/cassette/drawer and enter or update its contents. The user may enter information comprising medicine name, a unit of measure associated with the medicine, an expiration date, and a quantity. The same user interface may also be used to update quantities after a cart is restocked. An exemplary flow chart of the restocking process is shown in FIG. 16. In the example shown, users associated with a pharmacy confirm the layout of the cart and then dispense medicines to the cart according the inventory of the cart defined in the system. The user then enters information into the system that reflects restocking actions performed.

Figure 17:
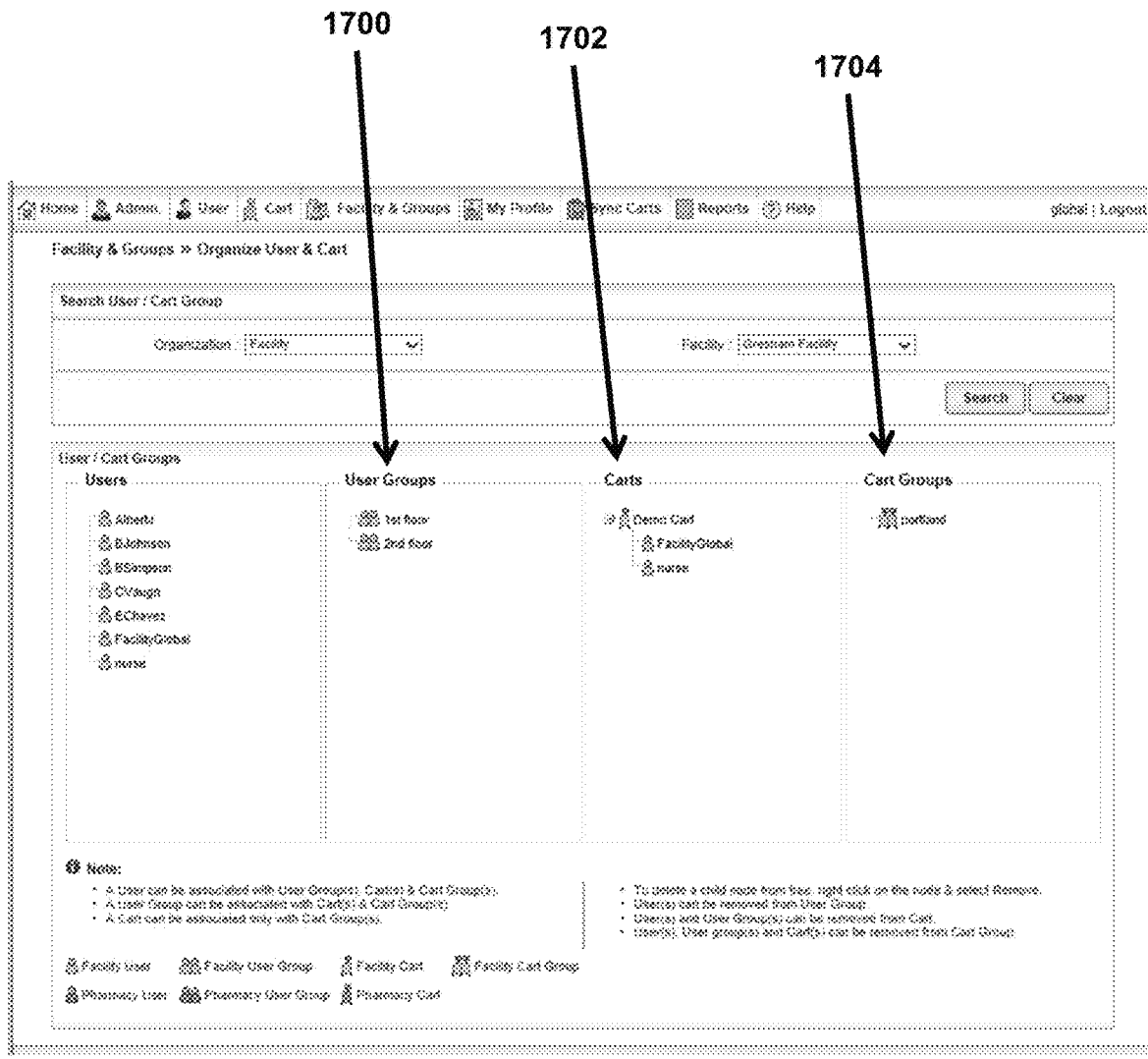
FIG. 17 is a screenshot of an exemplary embodiment of a organize user and cart interface.
Figure 18:
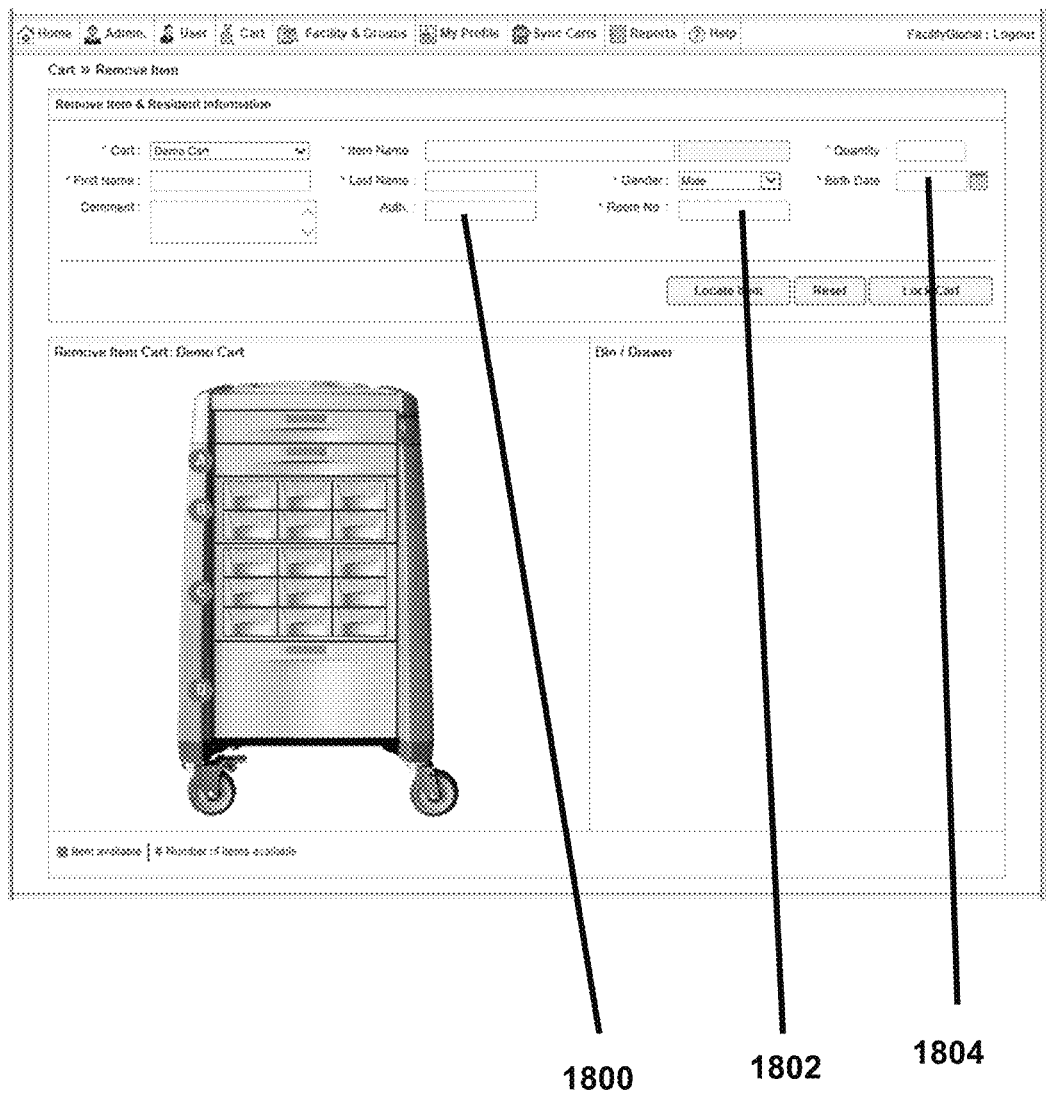
FIG. 18 is a screenshot of an exemplary embodiment of a dispense medicine user interface.
Figure 19:
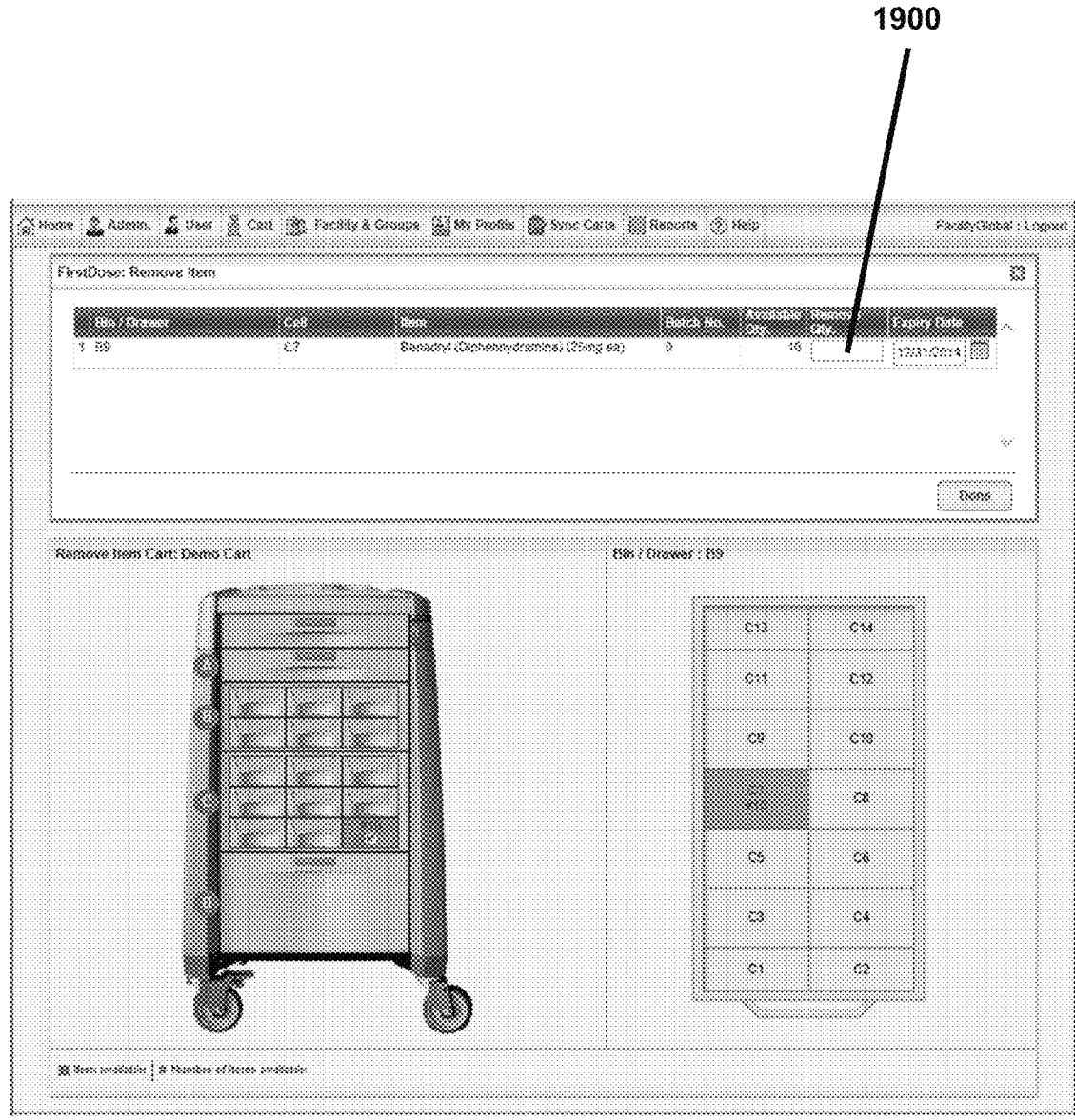
FIG. 19 is a screenshot of an exemplary embodiment of a dispense medicine user interface showing the bin identifier window.
Figure 20:
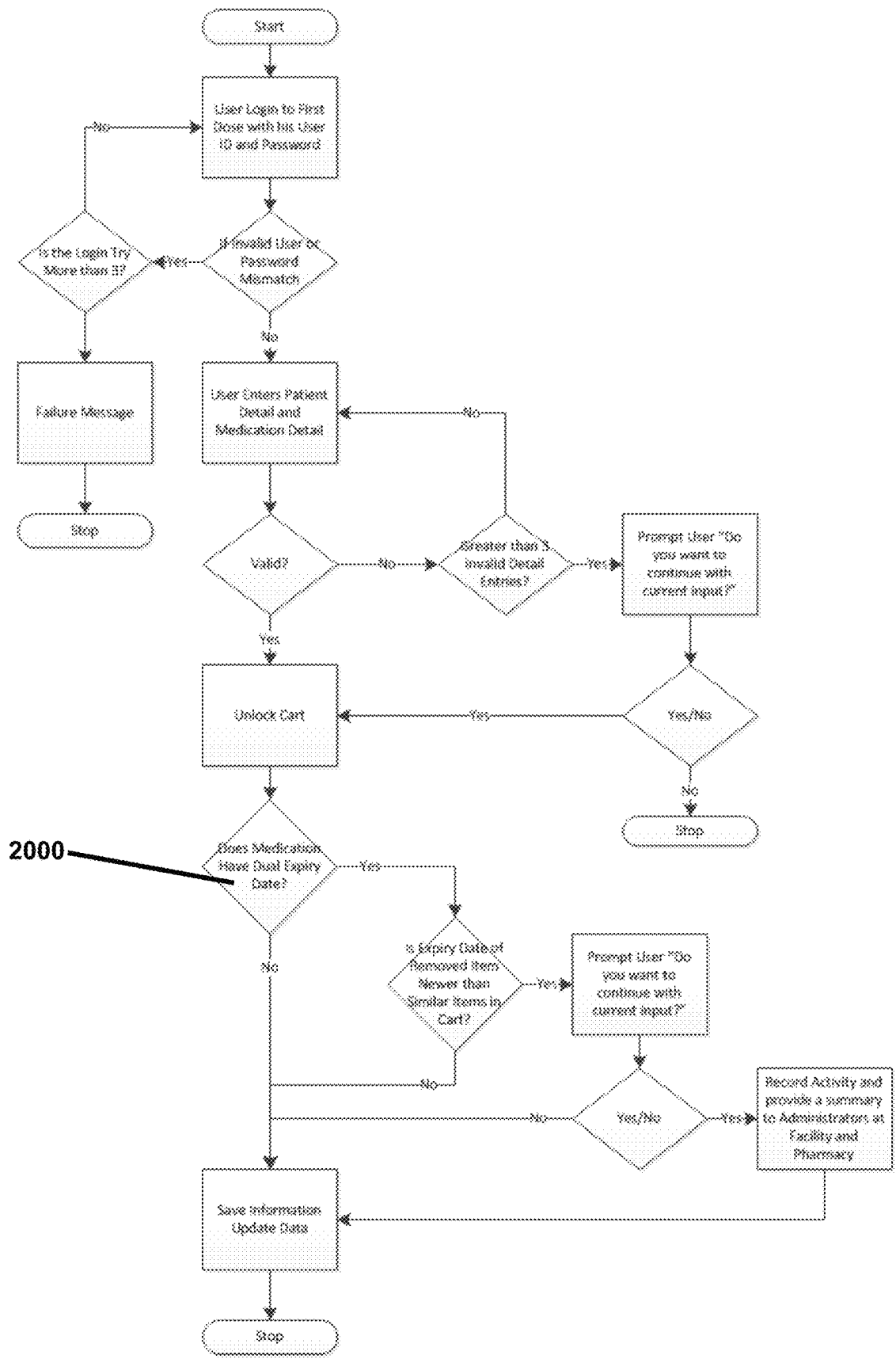
FIG. 20 is a flow diagram of an exemplary embodiment of the logic for performing a dispense medicine process.

Users may be added or removed from a cart by an administrative user. FIG. 17 illustrates a user interface that allows an administrator to view user relationships to carts. Users may be assigned to groups 1700 which may also be assigned to carts 1702. Carts, users and user groups may also be assigned to cart groups 1704. A super administrator may have access to all users and all carts when assigning users to carts. A facility administrator may only be provided with access to users and carts assigned to their same facility, Referring to FIGS. 18 and 19, when a user wishes to dispense a drug to a care recipient, the user may enter information comprising patient name, medicine, and quantity into a Medicine Dispense user interface. Additional details can be configured by a super administrator to be required by users when requesting item removal, such as an authorization number or code 1800, the patient's room number 1802, and the patient's birth date 1804. When the user enters this information, the system may provide a graphic illustration of where the drug is located on the cart. When the user removes the medication from the location shown, that user may enter the quantity 1900 of the medication removed in the user interface. FIG. 20 shows an exemplary flowchart of the dispense function of the system. The user may log into the system and enter the patient and medicine information. When this information is entered correctly, the system may cause the cart to allow a user access to a storage location from which the drug may be retrieved by such a user. An exemplary embodiment of the system may include an exception process 2000 to address the occurrence of multiple expiry dates for the same medicine within the same bin and or cart during the item removal process.

Figure 21:
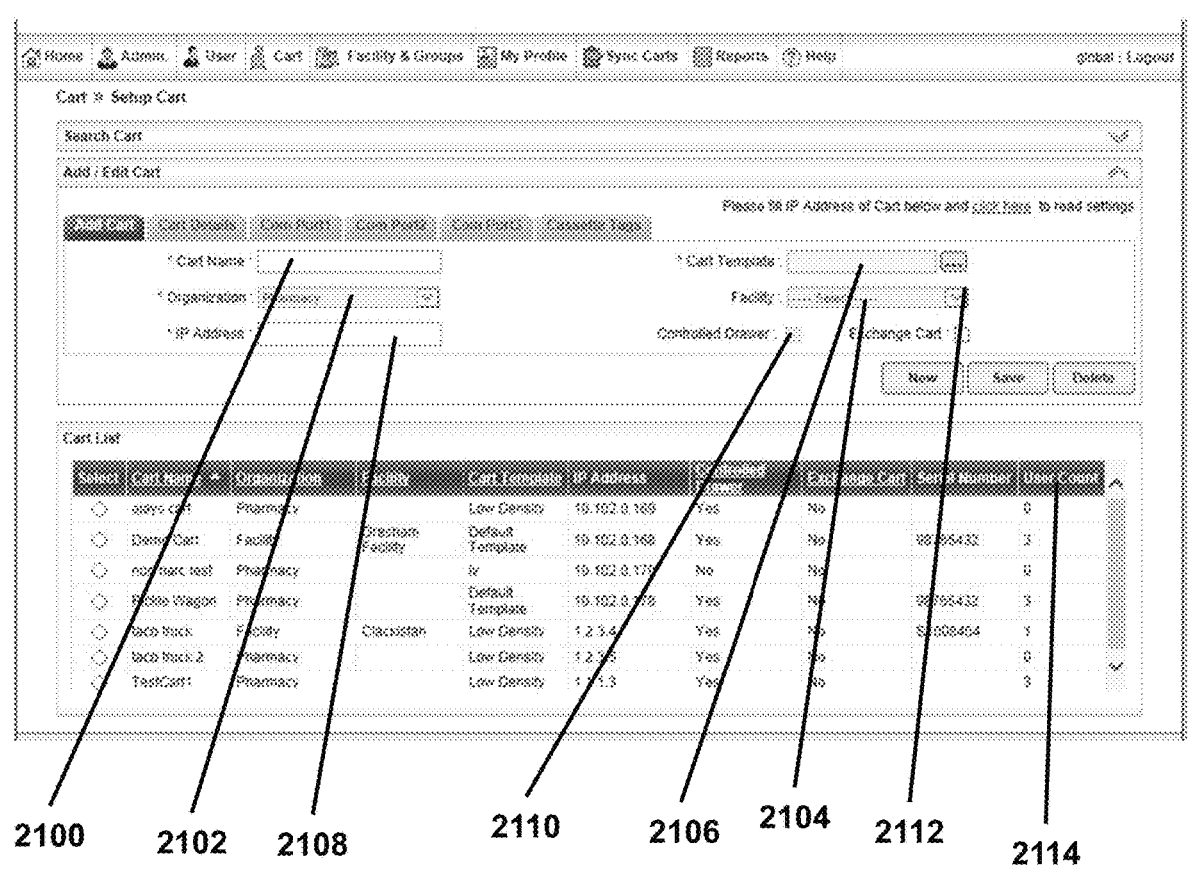
Figure 22:
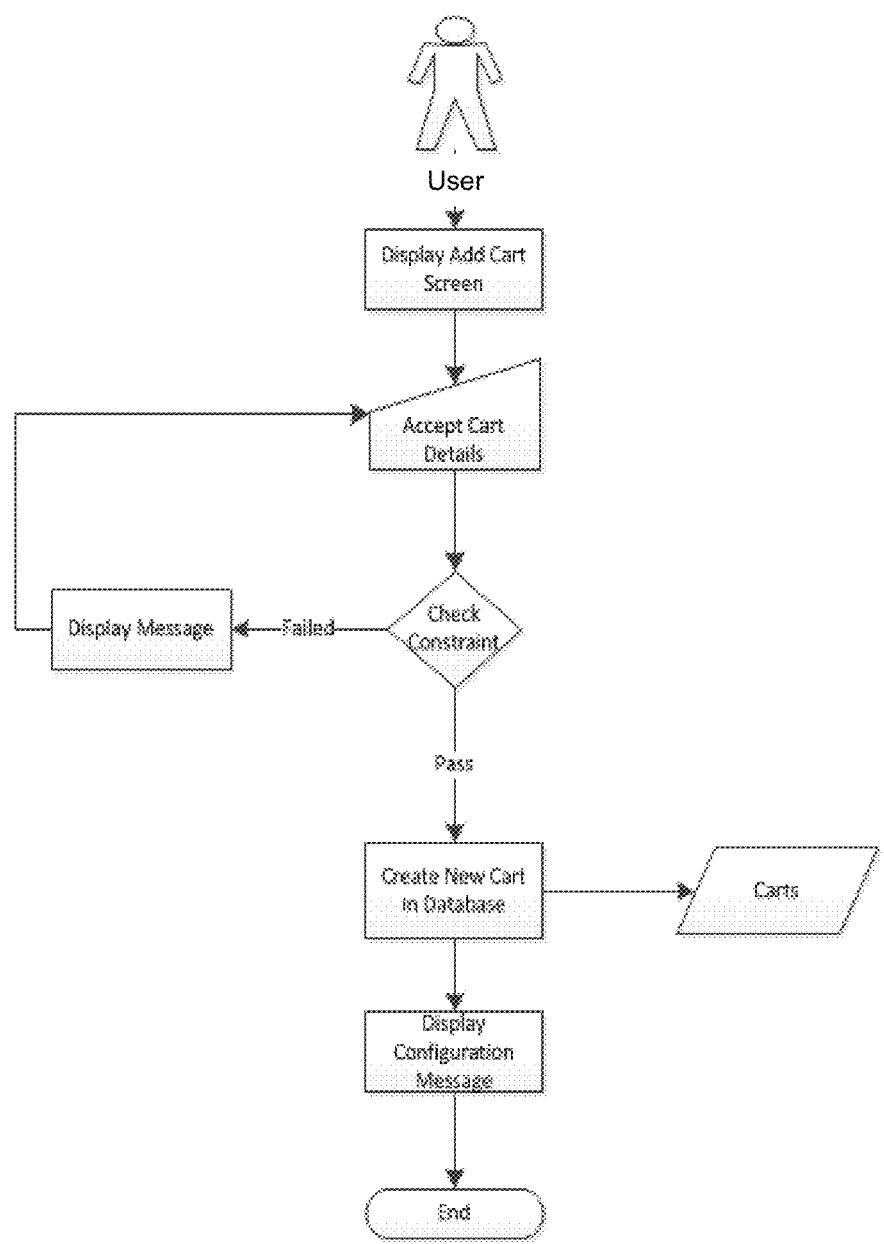
FIG. 22 is a flow diagram of an exemplary embodiment of the logic for performing an add a cart to the system process.

A user with administrative access to the system may have a need to view and edit the characteristics of a particular cart. Referring to FIG. 21, an administrative user may access a setup carts user interface that displays a listing of carts contained in the database 104 associated with the system. Information presented to the user in such a user interface may comprise cart name 2100, the organization 2102 the cart is associated with, the specific facility the cart is assigned to 2104, the cart bin organization template 2106, the serial number of the cart, an internet protocol address 2108 associated with the cart, an indication of whether the cart has a controlled access drawer 2110, if the cart is used a cassette exchange cart 2112, and the count of users assigned to the cart 2112. From this user interface, the system may allow an administrative user to add carts to the database and edit existing carts. FIG. 22 shows a flow chart of an exemplary embodiment of an algorithm for adding a cart to the system database.

Figure 23:
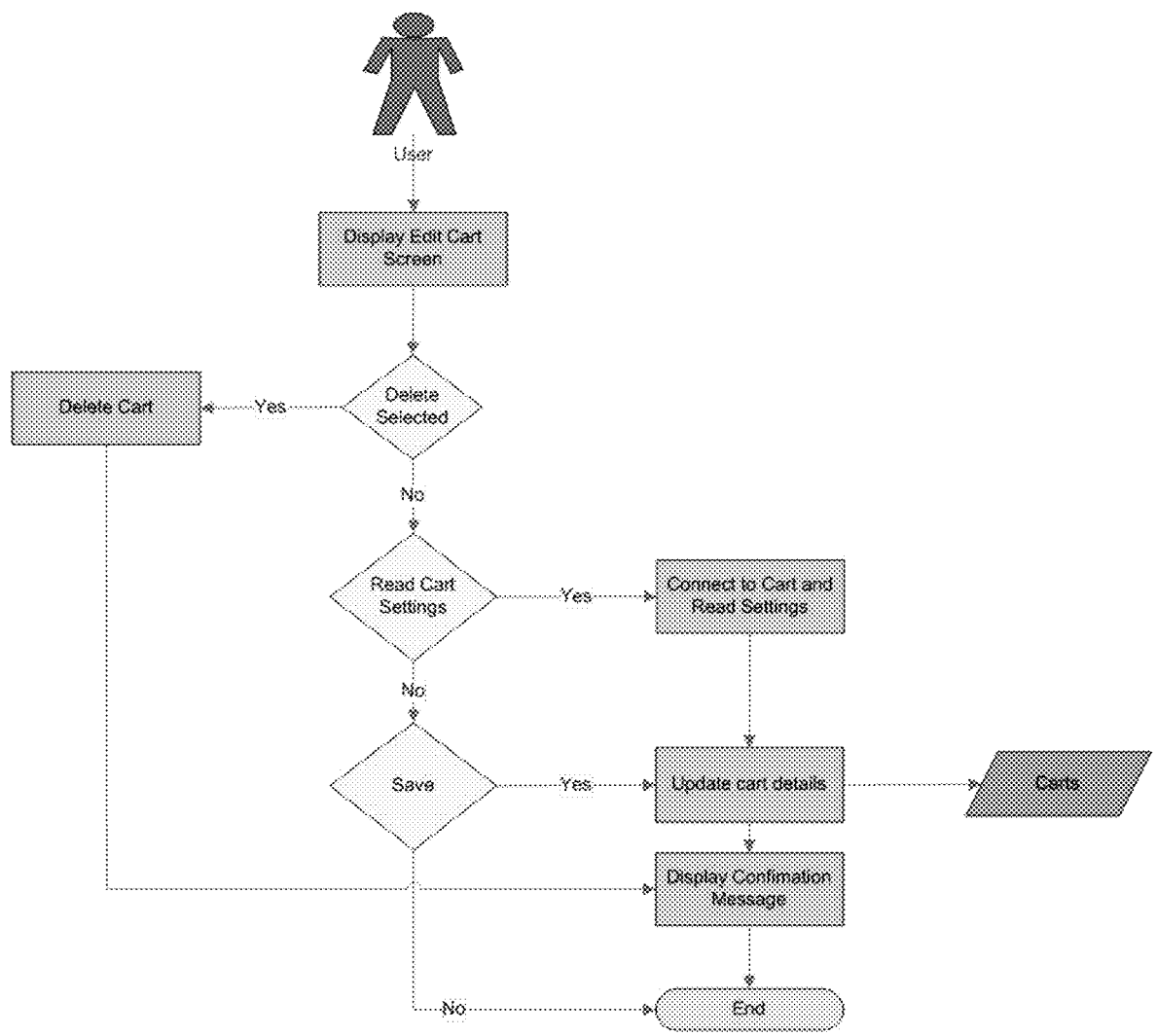
FIG. 23 is a flow diagram of an exemplary embodiment of the logic for performing an edit cart process.
Figure 24:
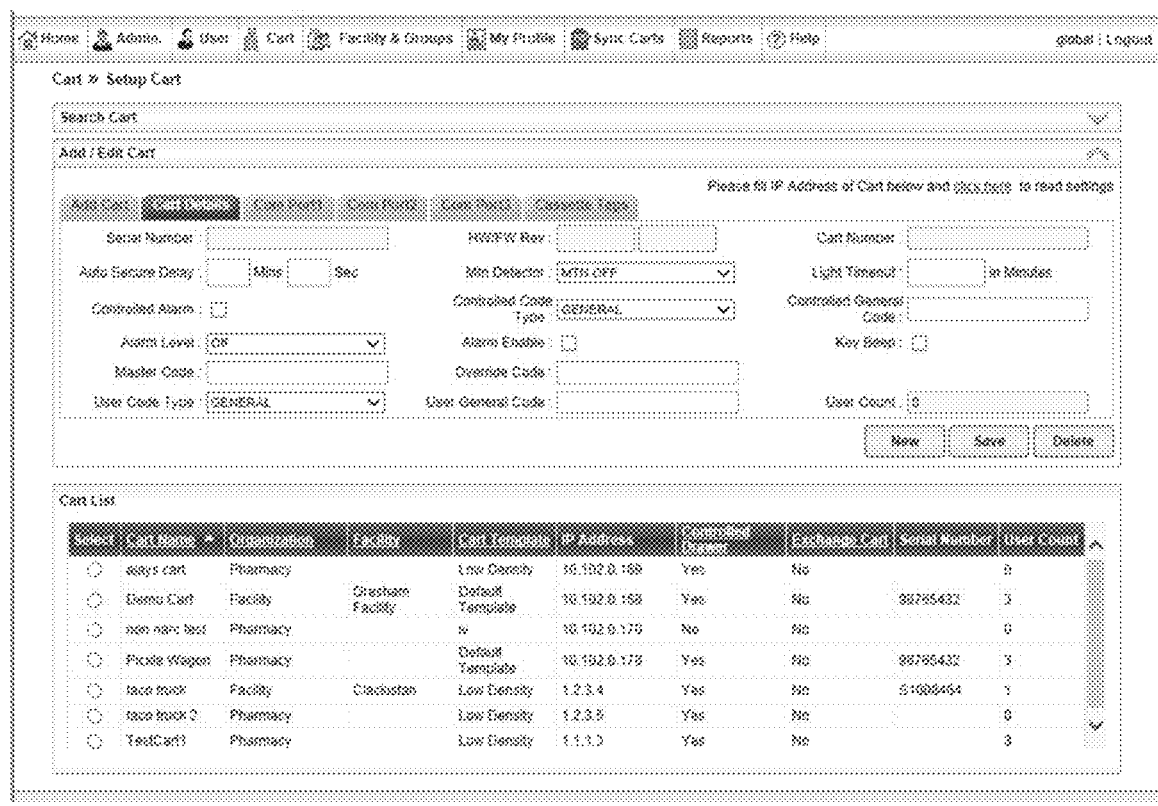
FIG. 24 is a screenshot of an exemplary embodiment of a setup carts user interface.

As described above, carts may contain equipment for communication with the system and also computer equipment. The carts may also comprise of subsystems which allow individual storage locations of the cart to be secured, alarms generated, and user interfaces provided which allow a user to interact with the cart or other components of the real time pharmaceutical control system. Characteristics of these subsystems may be modified through the use of an edit carts function of the Manage Carts algorithm. FIG. 23 shows a flow chart of an exemplary embodiment of an algorithm for editing cart characteristics. Referring to FIG. 24, an exemplary embodiment of a user interface of such an algorithm may allow an administrative user to adjust or display cart characteristics which may comprise key beeps, alert volumes, alarms, times during which a container remains accessible after unlocked, identification codes, user codes associated with the cart, and version numbers for cart software and hardware.

Figure 25:
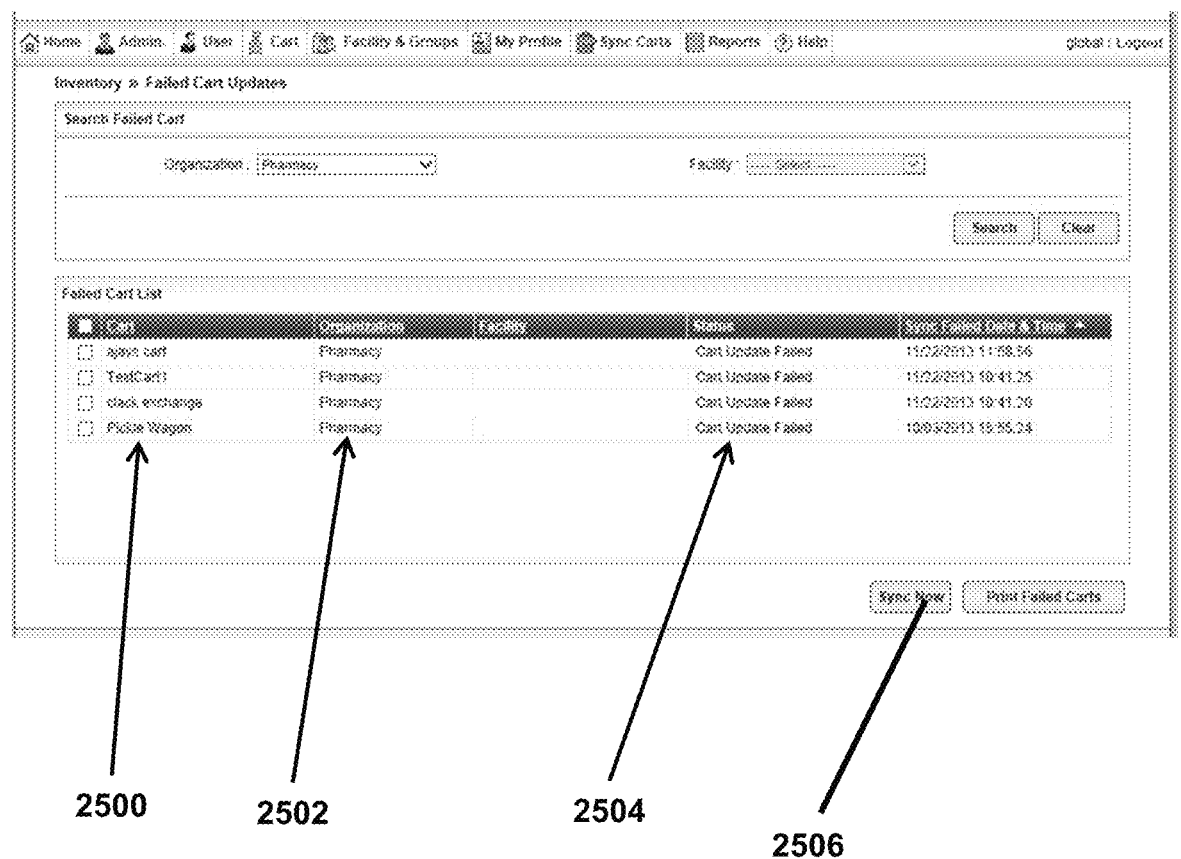
FIG. 25 is a screenshot of an exemplary embodiment of a failed cart update list user interface.
Figure 26:
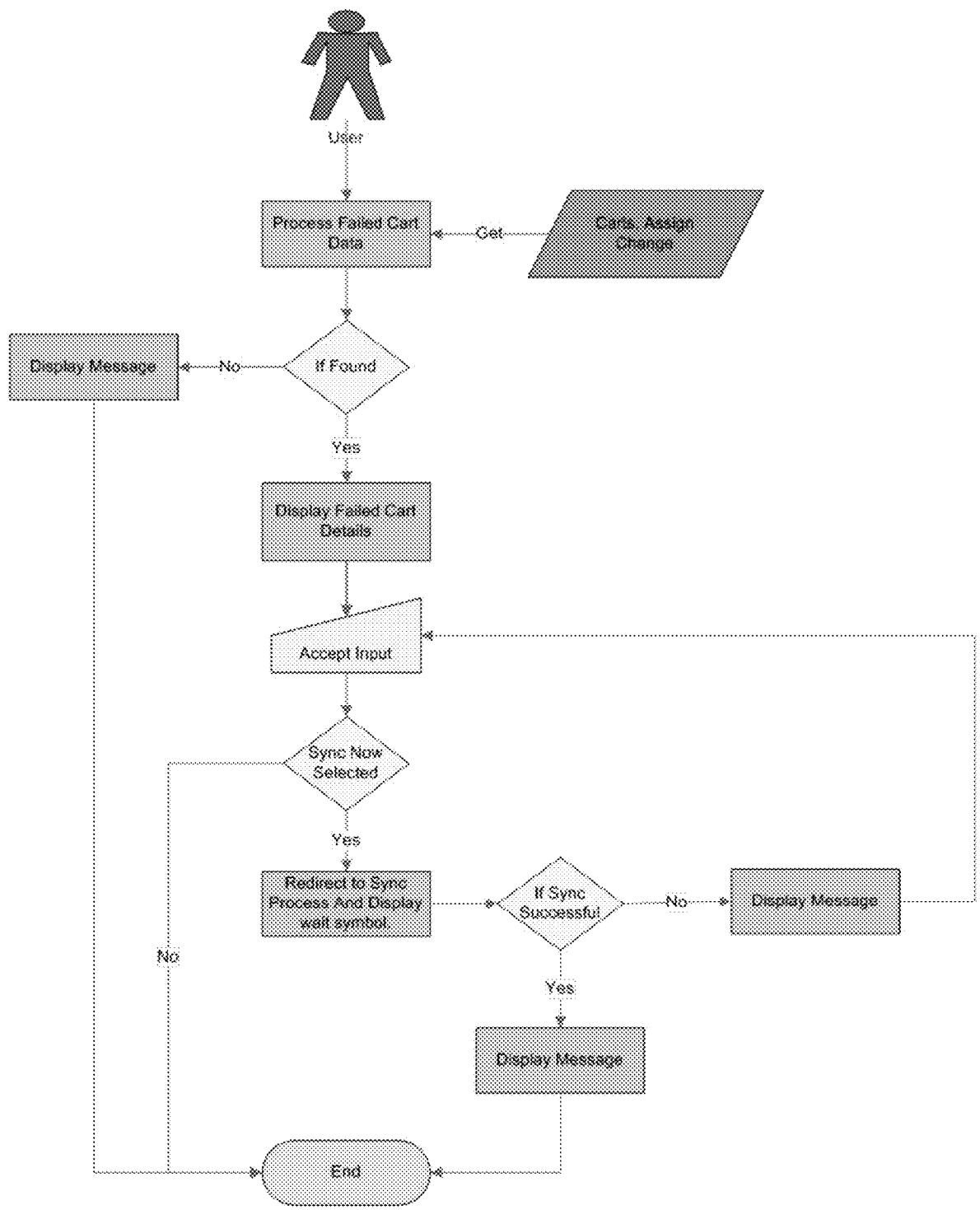
FIG. 26 is a flow diagram of an exemplary embodiment of the logic for performing a failed cart update process.

In order to allow carts to be moved from place to place when in use at a facility or pharmacy, communications between carts and the remaining components of the real time pharmaceutical control system may be interrupted from time to time. Because it may be beneficial for users to determine which carts are communicating and thus, synchronized with the system database 104 and conversely, which carts may have failed to communicate or update, the real time pharmaceutical control system may include an algorithm for identifying carts which have failed to communicate. An exemplary embodiment of the user interface of such a function is illustrated in FIG. 25. An example user interface may display cart name 2500 and group information 2502 as well as additional detail related to the cause of the communication failures 2504. A user may have the option to attempt to synchronize carts presented within the user interface as shown at 2506. An exemplary flow chart of such an algorithm is shown in FIG. 26.

Figure 27:
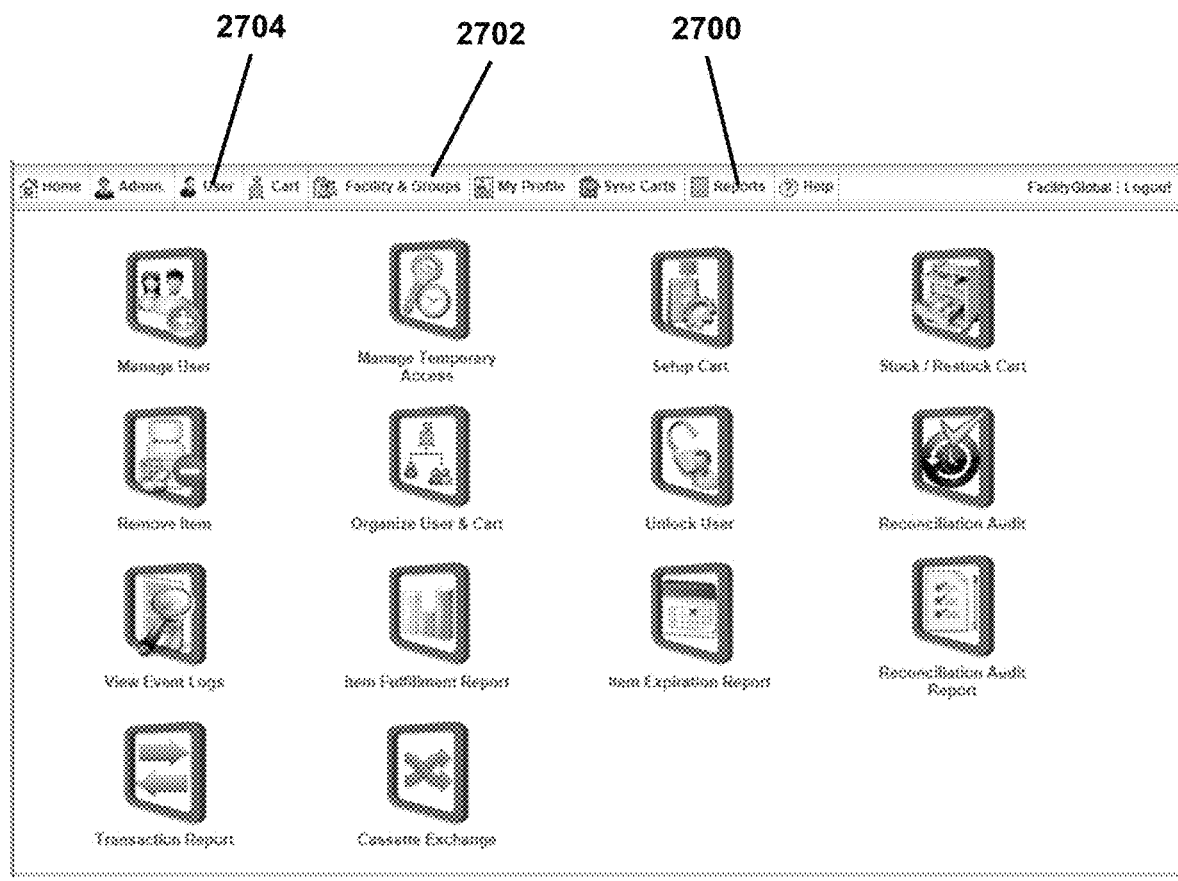
FIG. 27 is a screenshot of an exemplary embodiment of a site administrator user interface.

As was described earlier, a facility may have one or more users who have been granted administrative rights. Such rights may be less than those of a super administrator associated with the pharmacy and as a result, such a user may be presented with a user interface which offers fewer options for monitoring, editing, and reporting than would be found on a user interface intended for a super administrator. Referring to FIG. 27, a user interface for a facility administrator may comprise options for user setup 2704, user group setup 2702, user cart assignments, and reporting functions 2700 which provide information about cart inventories and cart events associated with that administrator's facility.

Figure 28:
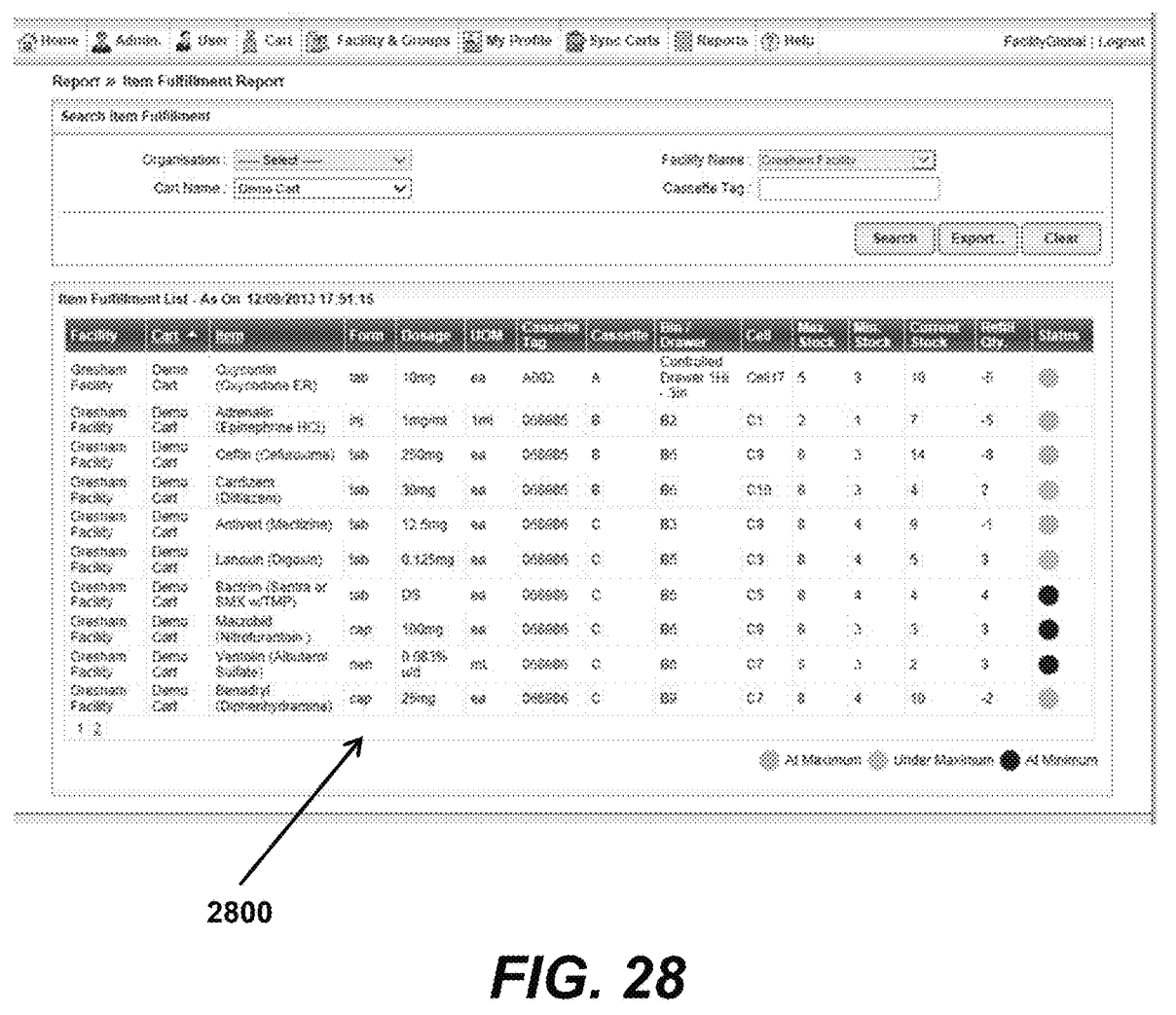
Figure 29:
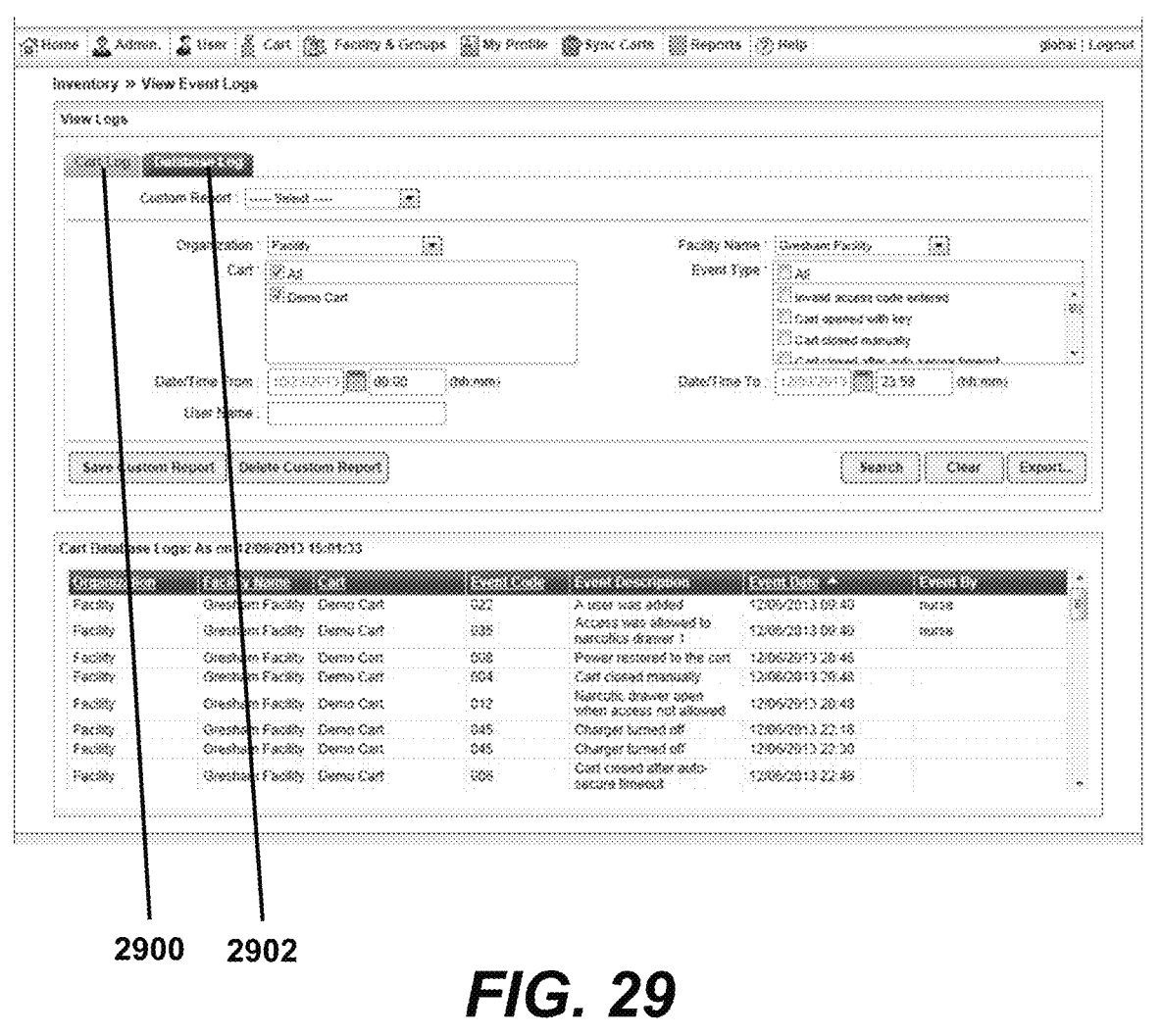

An exemplary user interface for a cart inventory reporting function is shown in FIG. 28. From such an interface, a user may view and print an inventory report 2800 associated with a cart. Such a report may comprise information such as medicine name, quantities, and expiration dates. Referring to FIG. 29, a user may also review cart log 2900 and database log 2902 files which display various types of information concerning access and user information associated with a cart and user operations. Such log files may contain data sourced from the database 104 and access control and log hardware 206 located on the cart.

Figure 30:
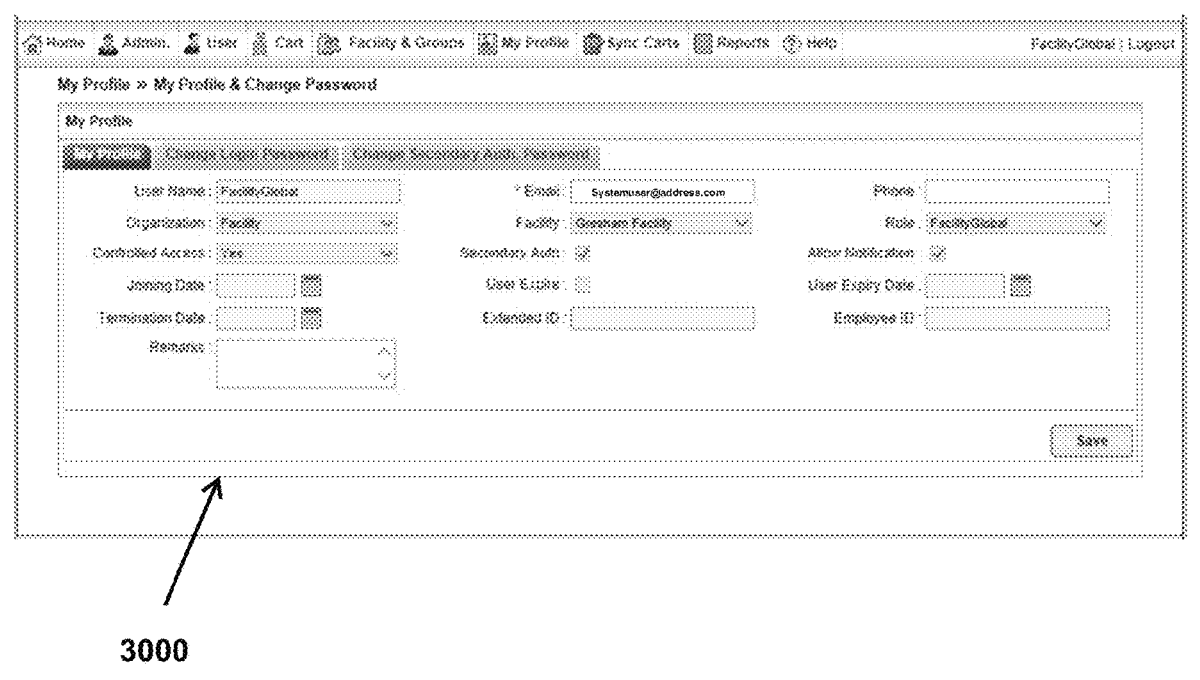
Figure 31:
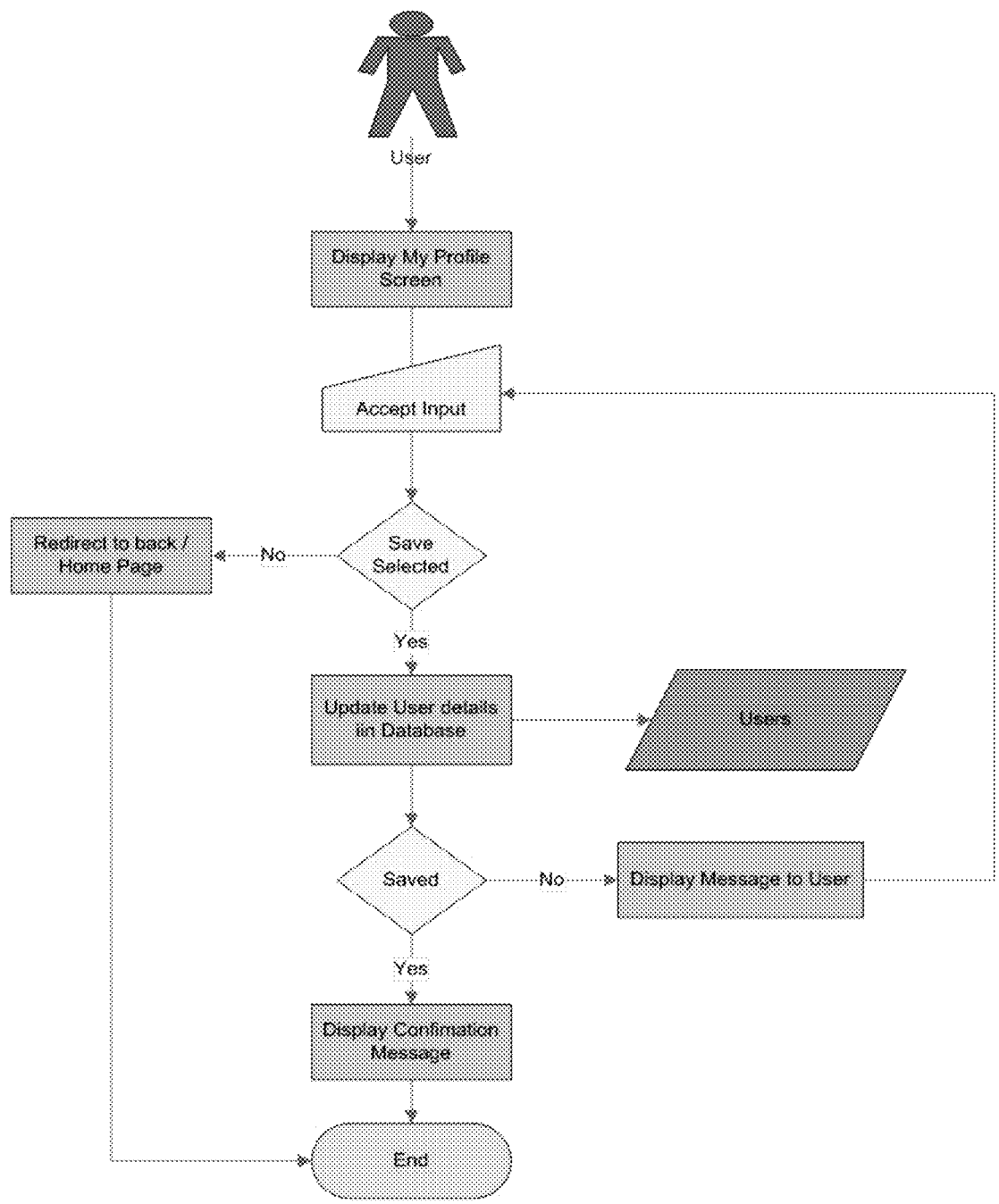
FIG. 31 is a flow diagram of an exemplary embodiment of the logic for performing a manage my profile process.

Even though configuration and maintenance functions may be restricted primarily to users with administrator or super administrator permissions, users without administrator provisions may nonetheless be provided the capability to view and edit certain pieces of information contained in the system database 104 used by the real time pharmaceutical control system. Referring to FIG. 30, when a user logs into the system, he or she may access such a manage user profile user interface 3000. The system may limit what information is presented on such a user interface depending upon the permission levels associated with a particular user. In an example embodiment of the system, a user may have the ability to edit his or her access ID, password, and email. A user may use the interface to review which carts he or she associated with and what user groups that he or she has been assigned. The system may require unique user names and provide the user feedback regarding his or her selected user name in order to maintain unique user name for all users of the system. An exemplary flow chart of such an algorithm is shown in FIG. 31.

Figure 32:
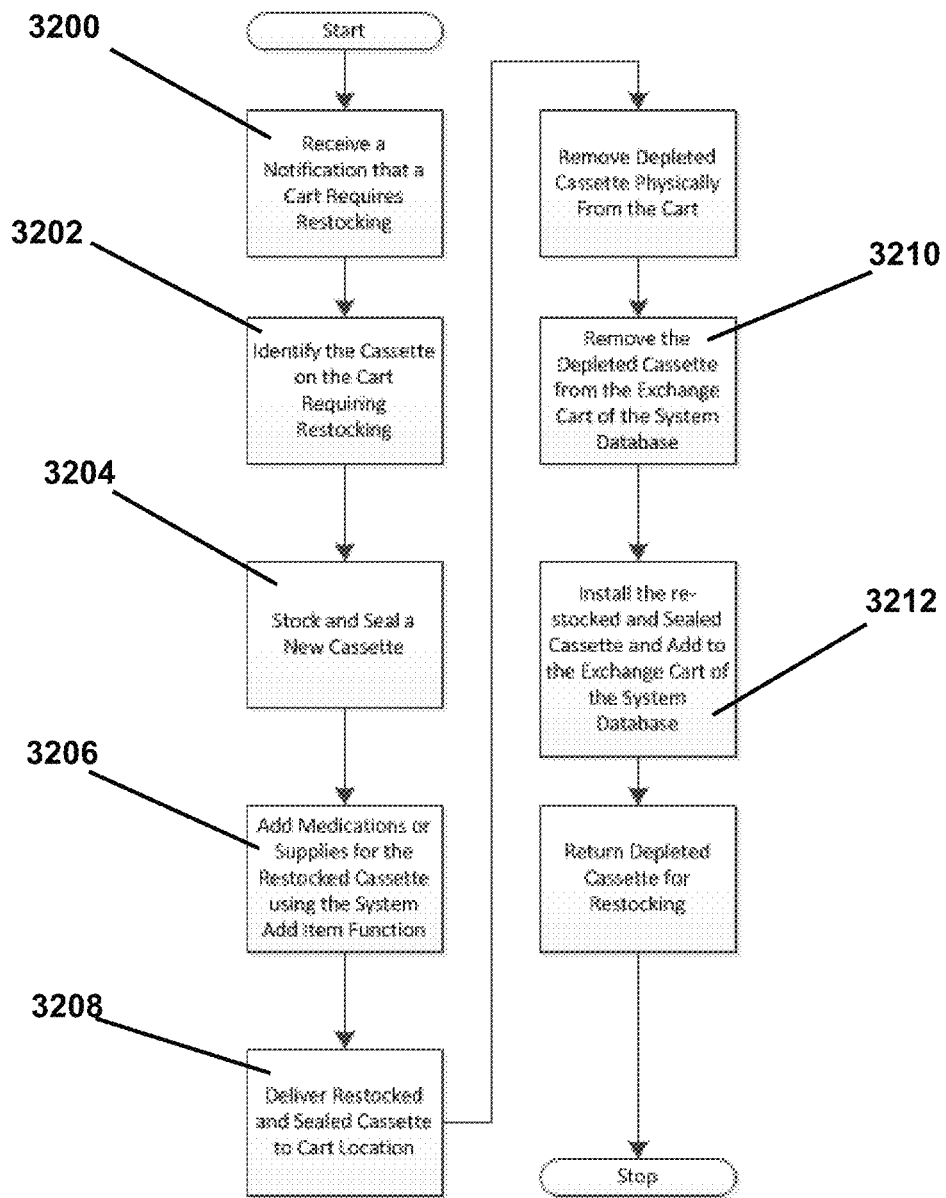
FIG. 32 is a flow diagram of an exemplary embodiment of the logic for performing a cassette exchange restocking of a cart.

An alternate cart restocking method may be employed by swapping entire cassettes containing bins or drawers or stand alone drawers. In such an embodiment, fully stocked cassettes or drawers may be exchanged for the cassette or drawer units with depleted stock installed in the carts. Referring to the flow chart of FIG. 32, a notification may be received that a cart requires a restocking of inventory 3200. A pharmacy or other supplier of cart contents may receive such a request and identify the cassette located on a cart that requires replenishment 3202. A replacement cassette may be located and stocked appropriately by a pharmacist or other licensed personnel. After the replacement cassette is restocked, it may be sealed for transport 3204. The materials added to the restocked cassette may be entered into the database 104 using the system add function 3206. The restocked cassette may then be delivered to the location of the cart requiring replenishment and installed 3208. After installing the replenished cassette, the partially depleted cassette may be returned to the pharmacy or supplier for future replenishment and reuse 3210. Such an embodiment may allow for delivery of a replenished cassette without the need for a pharmacist to travel to the site of the cart to perform the replenishment. The restocked cassette may be physically installed in the cart and the restocked cassette may be added to the cart contents in the database using a cassette exchange function 3212. Another application for such a restocking method may be cart drawers or storage areas that contain controlled substances such as narcotic drugs. Using such a method, controlled substances may be replenished in sealed containers and those containers installed in the cart needing replenishment. As with the cassettes previously described, such a method may allow for restocking without the need for a pharmacist to travel to the location of the cart.

Figure 33:
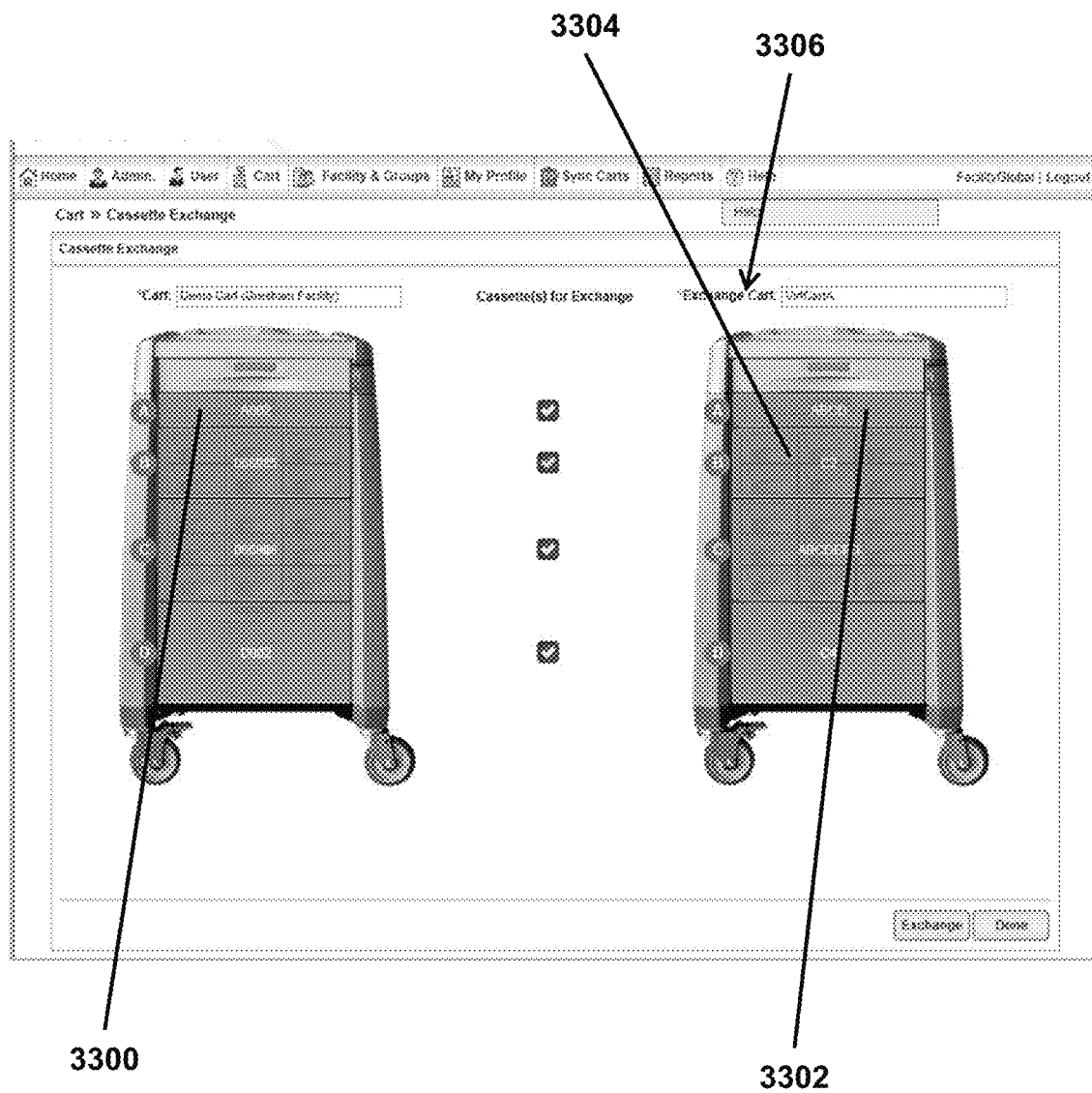
FIG. 33 is a screenshot of an exemplary embodiment of a cassette exchange user interface.

An exemplary embodiment of a user interface for a cassette exchange algorithm is shown in FIG. 33. One or more of the cassettes may be exchanged at one time. As illustrated, a first cassette 3300 may be exchanged for a second cassette 3302 from a cart or location designated as an exchange cart 3304. An exchange cart 3304 need not be an actual cart and may be a virtual cart used in the system to track replacement cassettes. In such an embodiment cassettes 3306 which may comprise a plurality of drawers or compartments may also be exchanged. The units removed from the carts may then be restocked using the restocking method described earlier.

It will be immediately recognized by those of skilled in the art that creating a system with an embodiment similar to that described herein may improve the efficiency of delivering preliminary medications to care recipients during periods of time when care providers may be waiting for recipient specific inventory to arrive from a pharmacy, reducing the time spent inventorying and reconciling storage containers. Because pharmacies are frequently not able to invoice a care provider for such preliminary medications until after an inventory has taken place, a system such as described herein may improve a pharmacy's cash flow by reducing the time period required to generate invoices for drugs consumed by a care provider. Having shown and described a preferred embodiment of the invention, those skilled in the art will realize that many variations and modifications may be made to affect the described invention and still be within the scope of the claimed invention. Thus, many of the elements indicated above may be altered or replaced by different elements which will provide the same result and fall within the spirit of the claimed invention.

What is claimed is:

1. A system for providing a user with remote access to pharmaceuticals, the system comprising:
   a cart comprising:
      a plurality of apertures which accept cassettes, wherein each cassette comprises a number of lockable bins, each of which are configured to receive one or more inventoried pharmaceuticals;
      a cart CPU configured to receive inventory data representing the lockable bin where each respective inventoried pharmaceutical is stored and user input identifying certain of said inventoried pharmaceuticals as requiring a one time access code (OTAC) for dispensation, wherein said cart CPU is configured to identify, based upon said inventory data and said user input, each of the lockable bins containing one or more of the certain of said inventoried pharmaceuticals requiring a OTAC for dispensation;
      a user interface placed in electrical communication with the cart CPU and configured to receive a user login request as well as a user request to access one of the lockable bins containing one or more of the certain of said inventoried pharmaceuticals requiring a OTAC for dispensation; and
      a network connection device in electrical communication with the cart CPU;
      wherein said cart CPU comprises software instructions, which when executed configure the cart CPU to generate a prompt at the user interface requesting the user to enter a username and password upon attempted access to the cart, and generate a second prompt at the user interface requesting the user enter a OTAC following receipt of a valid username and password and upon attempted access to one or more of the lockable bins identified by the cart CPU as containing one or more of the certain of said inventoried pharmaceuticals requiring a OTAC for dispensation;
   a remote database which is capable of electronic communication with the cart through the network connection device; and
   a remote CPU positioned at a pharmacy and capable of electronic communication with the database and configured to receive a OTAC request from the cart CPU comprising the valid user name, transmit OTACs electronically to the remote database to produce a stored OTAC, and transmit the OTAC to a phone or email server based on contact information stored at the remote database associated with the valid user name, wherein each of said OTACs are associated with a particular inventoried pharmaceutical;
   wherein said cart CPU comprises additional software instructions, which when executed configure the cart CPU to provide limited one time access to the bin containing the inventoried pharmaceutical associated with the OTAC only when the cart CPU receives a OTAC from the user interface that matches the stored OTAC;
   wherein the OTAC is an automatically generated, unique alphanumeric string of characters.

2. The system of claim 1 wherein:
the network connection is a wireless network connection.

3. The system of claim 1 wherein:
the OTAC's are unique to each patient.

4. A method for providing real time access to pharmaceuticals through a remote pharmacy system, the method comprising the steps of:
   providing a cart which accepts cassettes wherein each cassette comprises a number of individually lockable bins that each contain a specific type of itemized pharmaceuticals, a cart CPU comprising data representing the itemized pharmaceuticals stored in each of the number of individually lockable bins and data representing itemized pharmaceuticals requiring a one time access code (OTAC) for dispensation and a user interface;
   receiving a request to access the cart at the cart CPU from the user interface, wherein said request comprises a username and password;
   matching the received username and password to a stored username and password;
   receiving a request at the cart CPU from the user interface to dispense an itemized pharmaceutical for a particular patient;
   determining that the requested itemized pharmaceutical is one requiring a OTAC for dispensation;
   electronically generating a request for a OTAC at the cart CPU which comprises a request for one time access to a specific pharmaceutical for a specific patient;
   electronically transmitting the OTAC request to a remote CPU located at the remote pharmacy system, wherein said OTAC request comprises the received user name;
   determining, at the remote CPU, that the OTAC request is valid;
   generating a OTAC at the remote CPU;
   transmitting the OTAC electronically to a remote database and storing it to produce a stored OTAC;
   providing the OTAC to the user by way of cellular text message, email, or telephone call based on contact information stored at the remote pharmacy system associated with the received user name from the OTAC request;
   receiving a code at the cart CPU entered by the user at the user interface;
   determining, at the cart CPU, that the accepted code from the user matches the stored OTAC;
   identifying, at the cart CPU, which of the lockable bins contains a pharmaceutical associated with the user's OTAC request; and
   unlocking the locking device associated with one of the identified lockable bins on a one time basis;
   wherein the OTAC is an automatically generated, unique alphanumeric string of characters.

5. The method of claim 4 further comprising the steps of:
electronically determining at the remote CPU that pharmaceuticals need re-stocked in an old cassette;
stocking a new cassette with re-stocked pharmaceuticals;
sealing the new cassette; and
transporting the new cassette while sealed.

6. The method of claim 5 wherein:
the step of electronically determining that pharmaceuticals need re-stocked is performed by accessing the database from the remote CPU.

7. The method of claim 5 further comprising the steps of:
removing pharmaceutical data from the database which represents the pharmaceuticals in the old cassette; and
accepting pharmaceutical data at the database which represents the pharmaceuticals in each individually lockable bin of the new cassette.

8. The method of claim 5 wherein
the step of stocking the new cassette is performed by a pharmacist while the step of transporting the new cassette is performed by someone other than a pharmacist.

* * * * *